(12) United States Patent
Sarver et al.

(10) Patent No.: US 12,035,970 B2
(45) Date of Patent: Jul. 16, 2024

(54) REAL-TIME DETECTION OF ARTIFACTS IN OPHTHALMIC IMAGES

(71) Applicant: Alcon Inc., Fribourg (CH)

(72) Inventors: Edwin Jay Sarver, Cookeville, TN (US); Max Hall, Bradenton, FL (US)

(73) Assignee: Alcon Inc., Fribourg (CH)

( * ) Notice: Subject to any disclaimer, the term of this patent is extended or adjusted under 35 U.S.C. 154(b) by 705 days.

(21) Appl. No.: 17/236,908

(22) Filed: Apr. 21, 2021

(65) Prior Publication Data

US 2022/0218197 A1    Jul. 14, 2022

Related U.S. Application Data

(60) Provisional application No. 63/135,125, filed on Jan. 8, 2021.

(51) Int. Cl.
*G06T 5/00* (2024.01)
*A61B 3/103* (2006.01)
*G06T 7/00* (2017.01)

(52) U.S. Cl.
CPC .............. *A61B 3/103* (2013.01); *G06T 5/00* (2013.01); *G06T 7/0012* (2013.01); *G06T 2207/20081* (2013.01); *G06T 2207/20084* (2013.01); *G06T 2207/30041* (2013.01)

(58) Field of Classification Search
CPC ......... A61B 3/103; G06T 5/00; G06T 7/0012; G06T 2207/20081; G06T 2207/20084; G06T 2207/30041; G06T 2200/24; G06T 2207/10016; G06T 2207/10056; G06T 2207/30168

USPC ......................................................... 382/128
See application file for complete search history.

(56) References Cited

U.S. PATENT DOCUMENTS 9,603,516 B2    3/2017 Sarver et al.
2021/0259546 A1*  8/2021 Santos Garcia ..... A61B 5/7264

OTHER PUBLICATIONS

Anonymous: "python—How can I use a pre-trained neural network with grayscale images?—Stack Overflow", Aug. 24, 2018 (Aug. 24, 2018), XP055898974, Retrieved from the Internet:URL:https://stackoverflow.com/questions/51995977/how-can-i-use-a-pre-trained-neuralnetwork-with-grayscale-images[retrieved on Mar. 8, 2022]p. 2.

(Continued)

*Primary Examiner* — Charlotte M Baker

(57) ABSTRACT

Certain aspects of the present disclosure provide a system for processing image data from an intraoperative diagnostic device in real-time during an ophthalmic procedure. The system comprises an image capture element that captures a grayscale image of a first size and an image processing element that scales the grayscale image from the first size to a second size. The system also comprises a two-stage classification model comprising: a feature extraction stage to process the scaled grayscale image and generate a feature vector based on the scaled grayscale image and a classification stage to process the feature vector and generate an output vector. The image processing element is further configured to determine an image quality of the obtained grayscale image based on the output vector for display to an operator and the image quality of the obtained grayscale image indicates a probability that the obtained grayscale image includes an artifact.

25 Claims, 18 Drawing Sheets

(56) References Cited

OTHER PUBLICATIONS

Perez, et al: "A lightweight deep learning model for mobile eye fundus image quality assessment", SPIE Proceedings; (Proceedings of SPIE ISSN 0277-786X], SPIE, US,vol. 11330, Jan. 3, 2020 (Jan. 3, 2020), pp. 113300K-113300K, XP060127698, DOI: 10.1117/12. 2547126.
Raj, et al: "Multivariate Regression-Based Convolutional Neural Network Model for Fundus Image Quality Assessment",IEEE Access, IEEE, USA, vol. 8, Mar. 20, 2020 (Mar. 20, 2020), pp. 57810-57821, XP011781230, DOI: 10.1109/ACCESS.2020.2982588.

\* cited by examiner

REAL-TIME DETECTION OF ARTIFACTS IN OPHTHALMIC IMAGES

CROSS-REFERENCE TO RELATED APPLICATIONS

The present application claims the benefit of and priority to U.S. Provisional Application No. 63/135,125, entitled "Real-Time Detection of Multilabel Image Artifacts in an Ophthalmic Instrument Using a Convolutional Neural Network/Deep Neural Network Model", and filed on Jan. 8, 2021, the entirety of which is incorporated by reference herein.

INTRODUCTION

Aspects of the present disclosure relate to systems and methods for detecting artifacts in image data used during surgical procedures, such as cataract surgery, which enables improved surgical outcomes for patients.

Cataract surgery generally involves replacing a natural lens of a patient's eye with an artificial intraocular lens (IOL). During cataract surgery, medical practitioners may utilize various image-based measurement systems to analyze the patient's eye in real-time and to assist with performing the cataract procedure—such as to ensure proper selection, placement, and orientation of an IOL for cataract intervention. However, artifacts present in imaging data of the patient's eye can lead to measurement errors that go unknown or unnoticed by a medical practitioner, and may consequently reduce the efficacy of such procedures and lead to poor patient outcomes. Often, such outcomes require additional surgical intervention.

Therefore, there is a need for improved techniques for performing image data processing and analysis during procedures, such as cataract surgery, which lead to improved surgical outcomes for patients.

BRIEF SUMMARY

Certain embodiments provide a system for processing image data from an intraoperative diagnostic device in real-time during an ophthalmic procedure. The system comprises an image capture element configured to capture a grayscale image of a patient's eye from the intraoperative diagnostic device, the grayscale image having a first size. The system further comprises an image processing element configured to obtain the grayscale image from the image capture element, scale the grayscale image from the first size to a second size, and preprocess the scaled grayscale image in preparation for classification. The system also comprises a two-stage classification model comprising a feature extraction stage configured to process the scaled grayscale image and generate a feature vector based on the scaled grayscale image, and a classification stage configured to process the feature vector and generate an output vector based on the feature vector. The image processing element is further configured to determine an image quality of the obtained grayscale image based on the output vector for display to an operator, and the image quality of the obtained grayscale image indicates a probability that the obtained grayscale image includes an artifact.

Another embodiment provides a method of processing image data obtained from an intraoperative diagnostic device in real-time during an ophthalmic procedure. The method comprises capturing a grayscale image of a patient's eye from the intraoperative diagnostic device, the grayscale image having a first size, obtaining the grayscale image from an image capture element, and preprocessing the grayscale image in preparation for classification by a two-stage machine learning model. The method further comprises generating a feature vector based on the preprocessed grayscale image with a feature extraction stage of the two-stage machine learning model and generating an output vector based on the feature vector with a classification stage of the two-stage machine learning model. The method also comprises determining an image quality of the obtained grayscale image based on the output vector for display to an operator. The image quality of the obtained grayscale image indicates a probability that the obtained grayscale image includes an artifact that interferes with a measurement by the intraoperative diagnostic device.

Another embodiment provides a method of training a two-stage machine learning model that identifies artifacts in images obtained from an intraoperative aberrometer during an ophthalmic procedure. The method comprises obtaining the images, generating feature vectors with a feature extraction stage of the two-stage machine learning model for each of the images, generating a feature matrix based on stacking the generated feature vectors, and training a classification stage based on the feature matrix. The trained classification stage generates an output for a processed image indicating a probability that the image includes an artifact.

Other embodiments provide processing systems configured to perform the aforementioned methods as well as those described herein; non-transitory, computer-readable media comprising instructions that, when executed by one or more processors of a processing system, cause the processing system to perform the aforementioned methods as well as those described herein; a computer program product embodied on a computer readable storage medium comprising code for performing the aforementioned methods as well as those further described herein; and a processing system comprising means for performing the aforementioned methods as well as those further described herein.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
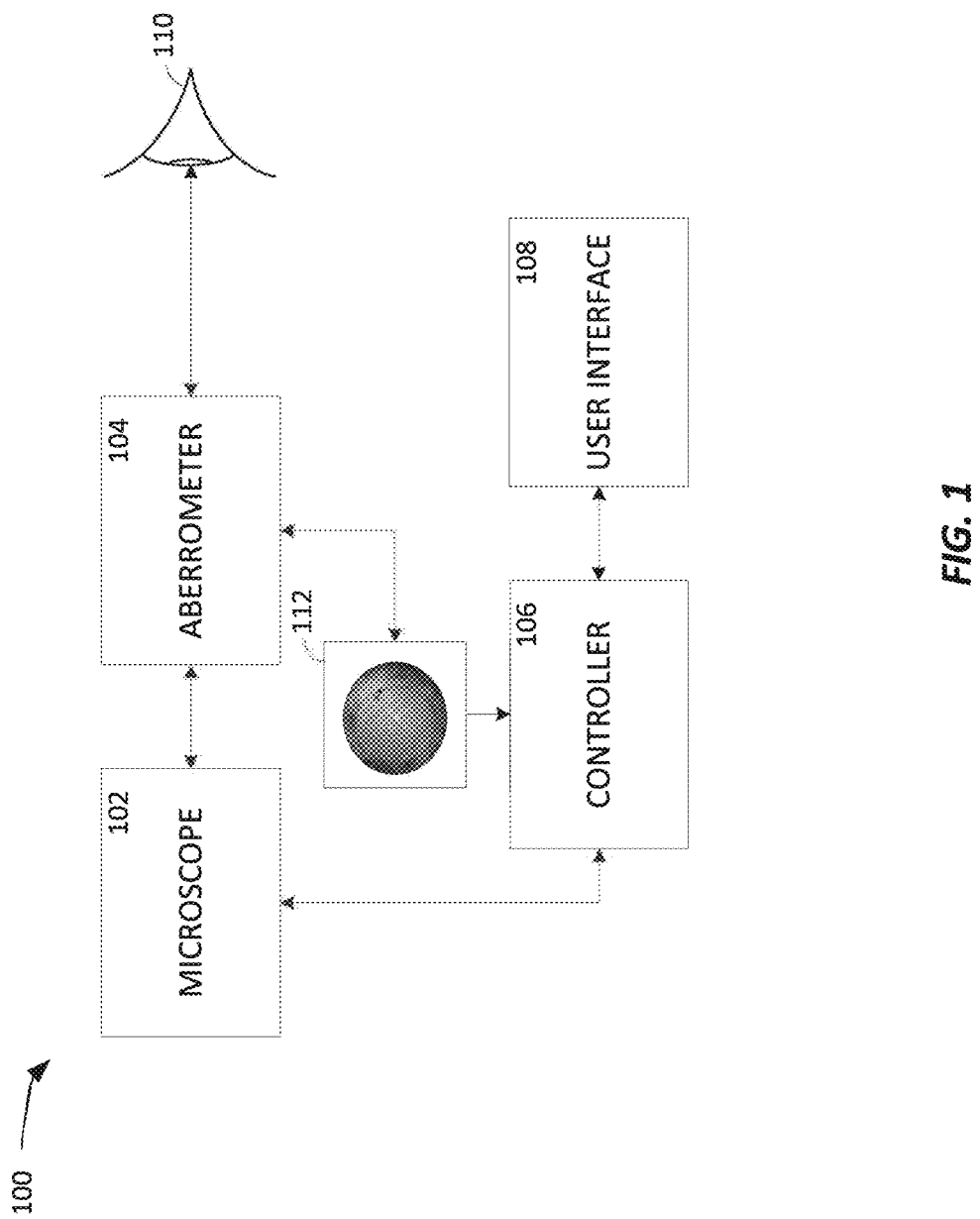
FIG. 1 depicts a block diagram of an imaging system for capturing digital images of a patient's eye during a surgical, diagnostic, or other procedure, in accordance with certain embodiments.

Aspects of the present disclosure provide apparatuses, methods, processing systems, and computer-readable mediums for performing image data processing and analysis during medical procedures. In various examples described herein, the medical procedures relate to the human eye, such as cataract surgery, and the images may be provided by a diagnostic device, such as an intraoperative aberrometer.

Intraoperative aberrometry is generally a process that allows surgeons to take refractive measurements in the operating room to aid in the determination of intraocular lens (IOL) power selection and placement. In some cases, an intraoperative aberrometry system may measure "wavefronts", which describe the propagation of light waves through a patient's eyes. In particular, an intraoperative aberrometer may be configured to identify aberrations (distortions) of light waves caused by irregularities of the patient's eye, which cause the light waves to converge onto the retina in an irregular manner. Cataracts are one such irregularity that causes suboptimal operation of the eye. Replacement of a patient's natural lens with, for example, an IOL, requires extreme precision to generate the best patient outcome. While tools such as intraoperative aberrometers are very effective to this end in principle, in practice, various common conditions can reduce their effectiveness and compromise a surgical intervention. For example, any visual artifact in image data generated and/or processed by an aberrometer, such as illumination glint, motion artifacts, floaters or bubbles in fluids of the eye, excess moisture or dryness in the eye, debris on optical equipment, and the like, can lead to refractive measurement errors, which in-turn lead to selection and placement errors and poor patient outcomes. Moreover, such visual artifacts may easily be overlooked by a practitioner busy managing a complex procedure, complex tools, and a patient all at once.

To resolve the shortcoming of conventional systems, and to enable more reliable refractive measurements, more precise surgical interventions, and better patient outcomes, embodiments described herein implement machine learning models (artificial intelligence) that analyze image data and identify artifacts that may reduce the quality of refractive measurements.

In addition to identifying such artifacts, embodiments described herein may proactively prevent refractive measurement errors by, for example, filtering image data (e.g., image data frames) that include identified artifacts. By filtering such data, measurement devices may beneficially be prevented from making inaccurate measurements and inaccurate determinations based on those measurements.

Further, embodiments described herein may proactively indicate to a medical practitioner the probability of, for example, artifacts in real-time image data being processed by an aberrometer based on real-time analysis by machine learning models. In various embodiments, systems described herein may be configured to generate graphical user interface elements to indicate detected artifacts, likelihood of measurement errors based on the detected artifacts, and the like. In this way, embodiments described herein offload this task from a practitioner and enable the practitioner to perform more precise procedures based on more accurate and complete information, resulting in better patient outcomes. Based on such graphical user interface elements and similar indications, the practitioner may adjust the system (e.g., adjust a camera angle of the aberrometer or the position of a patient's eye, clean an imaging sensor or component, reposition a tool used during the procedure, and so forth) in order to improve the quality of the image data and thereby to improve the quality and accuracy of refractive measurements.

Notably, in many cases, the systems and methods described herein may identify artifacts that are not readily (or not at all) identifiable by a medical practitioner using these systems. For example, artifacts that are small, dispersed, intermittent, fleeting, or the like, may be significant enough to cause refractive measurement errors, but may not be noticeable by even the best trained human practitioner. Accordingly, the systems and methods described herein provide a technical improvement over existing techniques that are not able to identify, indicate, and mitigate the presence of such artifacts.

Embodiments described herein may utilize a multi-stage machine learning model to identify artifacts in image data used by, for example, an intraoperative aberrometer. In one example, a two-stage machine learning model includes a first- or front-end stage configured to extract features from image data. The features may be, for example, created in the form of a feature vector. The two-stage machine learning model further includes a second- or back-end stage configured to perform classification. In some cases, the classification stage may be configured to generate an output vector indicating one or more probabilities that the image processed by the first-stage includes any artifact(s) based on the feature vector for the image. In combination, the feature extraction (i.e., first-) stage and the classification (i.e., second-) stage can detect one or more artifacts in processed image data.

Beneficially, a multi-stage model architecture (e.g., a two-stage architecture) allows for modular training and implementation of each stage separately. In this way, different (and improved) classification stages can be implemented without the need to retrain or redesign the feature extraction stage. This modularity in-turn improves (reduces) training time and resource usage so that the overall model may be easily and frequently evolved, which in-turn improves the intraoperative aberrometry systems described herein, and ultimately quality of procedures and patient outcomes.

Although the image analysis and classification systems, methods, and techniques herein are described with respect to one or more procedures performed intraoperatively with an intraoperative aberrometer, in certain embodiments, the image analysis and classification systems, methods, and techniques described herein can also be utilized pre- and/or postoperatively. For example, the image analysis and classification systems, methods, and techniques described herein can be utilized during a preoperative procedure to obtain measurements and images for preparing a surgical plan in preparation for a surgical procedure. Similarly, the image analysis and classification systems, methods, and techniques described herein can be utilized postoperatively, for example, to check and/or verify results from the procedure. Furthermore, the image analysis and classification systems, methods, and techniques described herein can be used with other optical imaging devices (for example, other than an aberrometer) preoperatively, intraoperatively, and/or postoperatively.

Example Intraoperative Imaging System

FIG. 1 depicts a block diagram of an example imaging system (referred to herein as system or imaging system) 100 for capturing digital images of a patient's eye 110 during a surgical, diagnostic, or other procedure. The system 100 includes a microscope 102, an aberrometer 104, a controller 106, a user interface 108, and a representation of a patient's eye.

The microscope 102 may comprise one or more optical features, viewing features, lighting features, and/or control features. The optical features may comprise one or more lenses for focusing light reflected by a target object being viewed through the microscope 102, such as the patient's eye, during any procedure described herein. Thus, the microscope 102 enables an operator (for example, a medical practitioner, such as a surgeon, nurse, assistant, specialist, and so forth) to view the patient's eye (or portion thereof) with greater magnification than viewing with the naked eye allows or with added features, such as identification or marking features and the like. The viewing features, which may comprise one or more of an eyepiece or a computerized interface, may include at least one optical channel having at least one optical lens disposed therein. The viewing feature may be either monocular or binocular and enables the operator to view the target object with increased magnification. One or more aspects of the optical features and/or the viewing features may be adjustable with regard to focusing of the optical features, the viewing features, the positioning of the patient's eye, and the like, as needed by the operator or in an automated manner. In some embodiments, the optical features and the viewing features comprise an optical pathway of the microscope 102.

The lighting features may comprise a light source configured to provide and/or project visible light into the optical pathway of the microscope 102. The lighting feature may be adjustable with regard to positioning, focusing, or otherwise directing the visible light as needed by the operator or in an automated manner.

The control features may enable the operator to manually activate and/or adjust other features of the microscope 102. For example, the control features may include components that enable adjustment of the lighting features (for example, controls to turn on/off the lighting feature and/or adjust a level of light, focus, and so forth). Similarly, the control features may include components that enable adjustment of the optical features (for example, to enable automatic or manual focusing of the optical features or movement of the optical features to view different targets or portions of the target or to change magnification of the target). For example, the control features may include knobs and similar components that enable adjustment of the optical features (for example, controls to move the optical components in a horizontal and/or vertical direction, to increase and/or decrease magnification, and the like). Further, the control features may include components that enable adjustment of the viewing feature, such as focusing elements, filtering elements, and the like. In some embodiments, the control features for the viewing feature are manually and/or automatically adjustable.

In some embodiments, the microscope 102 is used in conjunction with or replaced with one or more diagnostic devices. The operator may use the microscope 102 during any medical or diagnostic procedure to enlarge the patient's eye (or a portion thereof) for better visibility during the procedure. Additionally, the operator may use the microscope 102 (or other diagnostic device) to obtain one or more single and/or multi-dimensional images and/or other measurements of the patient's eye 110. The microscope 102 may comprise a three-dimensional stereoscopic digital microscope (for example, the NGENUITY® 3D Visualization System (Alcon Inc., Switzerland)). The one or more diagnostic devices may be any of a number of devices for obtaining and processing single and/or multi-dimensional camera-based (or similar) images and/or measurements of ophthalmic anatomy, such as an optical coherence tomography (OCT) device, a rotating camera (for example, a Scheimpflug camera), a magnetic resonance imaging (MRI) device, a keratometer, an ophthalmometer, an optical biometer, and/or the like.

The aberrometer 104 may include a light source that creates a beam of light that is directed into the patient's eye 110 via a combiner mirror or beam-splitter. The beam of light directed into the patient's eye 110 is reflected back into the aberrometer 104 from the patient's eye 110 and via the combiner mirror or beam-splitter. The reflected light beam is further reflected and refracted by the aberrometer 104 before being diffracted and formed into an image captured by the aberrometer 104. For example, the aberrometer 104 may include at least one camera, light detector and/or similar sensor configured to capture, record, and/or otherwise detect an image of the patient's eye and convert it into a computer-readable format. In some aspects, the at least one camera is not part of the aberrometer 104, but rather is a standalone component that generates the image of the patient's eye based on information received from the aberrometer 104, as described further below.

The aberrometer 104 (or other wavefront sensor or diagnostic device) may be positioned between the microscope 102 and the patient's eye 110. For example, the aberrometer 104 may include an optical device for reflecting light, such as the combiner mirror or beam-splitter. The optical device may selectively reflect portions of the electromagnetic spectrum (for example, infrared light portions of the electromagnetic spectrum) into the aberrometer 104 for processing, analysis, and/or measurement while allowing other portions of the electromagnetic spectrum (for example, visible light portions of the electromagnetic spectrum) to pass through the optical device and into the microscope 102 for viewing by the operator. Alternatively, though not shown in FIG. 1, the system 100 may include the optical device positioned between each of the aberrometer 104 and the microscope 102 and the patient's eye 110 so that light is directed into either the aberrometer 104 or the microscope 102 without passing through one into the other.

In some embodiments, the system 100 may include one or more camera and/or imaging systems (not shown in FIG. 1) configured to capture images of different views and/or perspectives of the patient's eye 110. In some instances, the one or more camera systems are each positioned at different locations relative to the patient's eye 110, the microscope 102, and/or the aberrometer 104. In some instances, different camera systems may use one or more different light sources (for example, light emitting diodes (LEDs), lasers, and the like) operating at different wavelengths (for example, in the visible light spectrum, the infrared spectrum, and the like).

In some instances, the one or more cameras may provide to the controller 106 a plurality of types or views of images. Each type of image or image view may capture different information and/or aspects of the patient's eye 110. For example, the plurality of image views or types may comprise a wide field view illuminated by light having wavelengths in the visible spectrum (of the electromagnetic spectrum), a focus view illuminated by LED light of 840 nanometer (nm) wavelengths, and an interferogram view illuminated by light of 740 nm wavelengths.

The combination of the microscope 102 and the aberrometer 104 enable viewing and measurement of the patient's eye 110 during planning and performing various procedures. The microscope 102 and the aberrometer 104 may each be focused at a point occurring, for example, at a surface of the patient's eye 110, such that a field of view of the aberrometer 104 overlaps, at least in part, a field of the microscope 102 and such that the patient's eye 110 remains positioned within overlapping portions of the fields of view during the procedure. In some instances, the microscope 102 and the aberrometer 104 are focused at substantially the same point, such that the center of each respective field of view is located at approximately the same point of the patient's eye 110. Thus, the operator can view the patient's eye 110 through the microscope 102 while the aberrometer 104 (and/or the one or more cameras) generates images of the patient's eye 110.

More specifically, the one or more cameras (either part of the aberrometer 104 or external to the aberrometer 104) may convert the information from the aberrometer 104 into a computer-readable format. The controller 106 may obtain the images from the camera and may measure and analyze the images captured by the one or more cameras (i.e., the information from the aberrometer 104 converted into the computer-readable format). The controller 106 may quantify characteristics of the captured images, and thus, the refractive properties of the patient's eye 110 examined during the procedure.

The different image views may capture different aspects of the patient's eye 110. In some embodiments, the wide field view may provide the operator with a complete view of a front of the patient's eye 110 and may enable centering of the patient's eye 110 in a field of view for each of the other view types. Such wide field view images of the patient's eye 110 may include one or more artifacts, which may indicate one or more conditions of which the operator or the system 100 may need to be aware. For example, the wide field view images may include artifacts caused by debris, for example, on an optical element or the combiner mirror/beam-splitter, or caused by an instrument used during the procedure being too close to the cornea of the patient's eye 110 (for example, a lid speculum instrument).

The focus view provides image capture of light generated by one or more light sources as it reflects off a cornea of the patient's eye 110. Such images may enable calculation of a distance of the system 100 (for example, a distance of the camera and/or the aberrometer 104) from the patient's eye 110. The focus view images may present artifacts due to fluid or hydration changes in one or more parts of the patient's eye 110. For example, the focus view images may include artifacts when light from one or more of the light sources spreads or "breaks up" due to drying of tear film on the anterior corneal surface of the patient's eye 110. In some instances, fluid pooling (from naturally developing or supplemented tears) causes light from the light sources to spread or elongate in a direction, causing a "legs" artifact. Furthermore, excess motion between even and odd frames as captured by the focus view images (for example, captured by an analog camera) may create an interleaving artifact of light reflections.

The interferogram view may enable capture of an image stream that, when processed, provides ocular aberration data including real-time refractions data to the operator. The interferogram view images may include artifacts caused by presence of bubbles captured in the image, illumination glint (which may correspond to increased reflection of light from the patient's eye 110), floating debris in the patient's eye 110, and general distortions on top of a normal Moire spot pattern.

Any image type and/or image captured by the aberrometer 104 or the imaging device may include any one or more of the above identified artifacts, or no artifact.

Figure 2A:
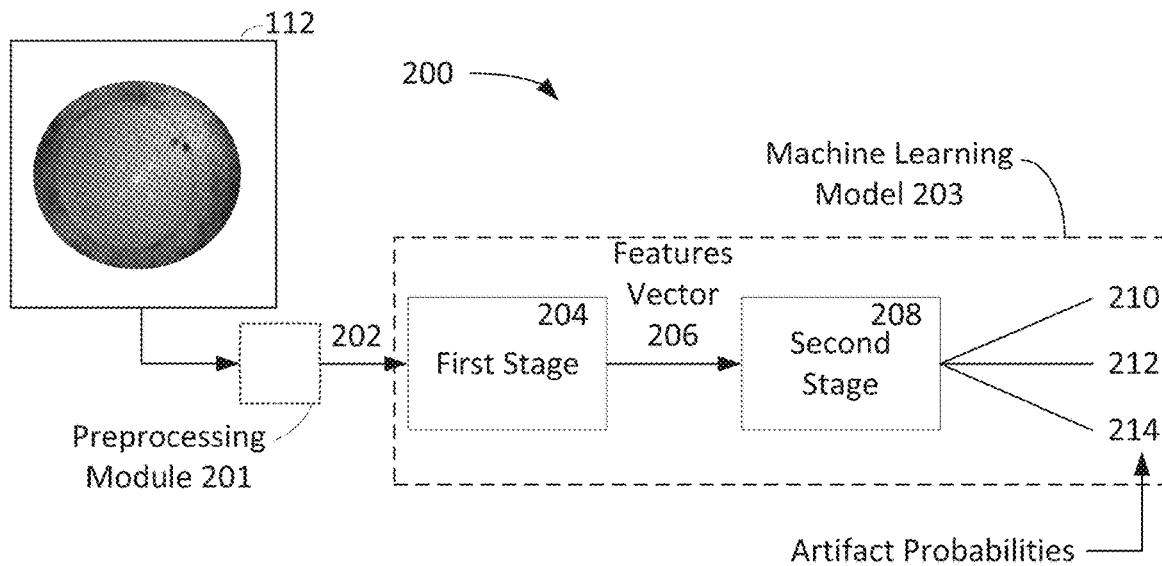
FIG. 2A depicts a data flow for processing an individual image with a machine learning model implemented by the system of FIG. 1, in accordance with certain embodiments.
Figure 2B:
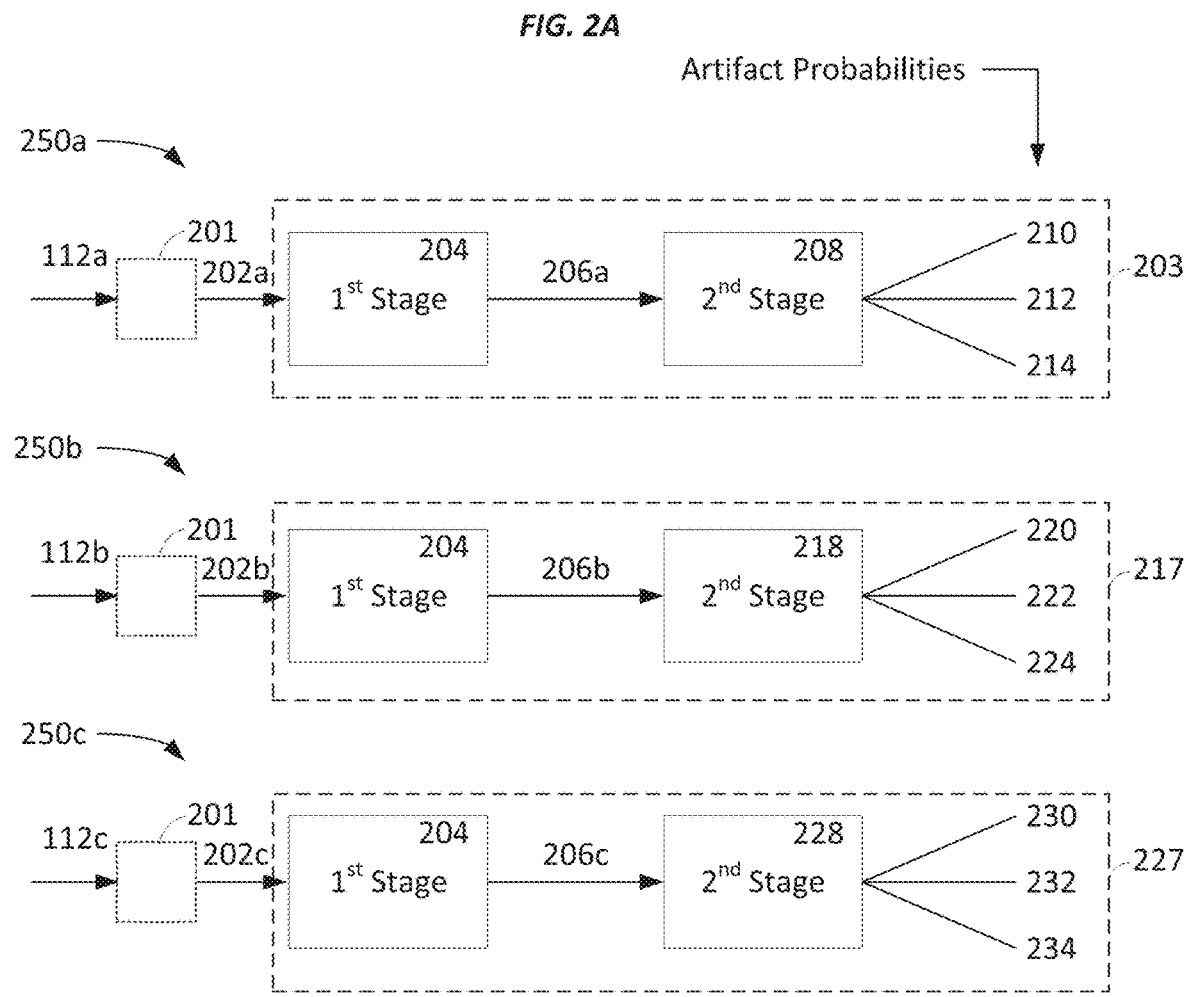
FIG. 2B depicts a set of data flows for processing multiple images with different machine learning models, in accordance with certain embodiments.

The controller 106 may identify whether an image includes one or more artifacts by applying one or more machine learning models, as described for example with respect to FIGS. 2A and 2B. The machine learning model(s) may generally include a feature extraction stage for generating predictive features based on the data received by the controller 106, and a classification stage for predicting whether various artifacts are in the received data (e.g., image data artifacts). One or both of the feature extraction stage and the classification stage may be trained and optimized based on a repository of previously captured images (for example, images from previous procedures). The repository may include images manually classified (for example, labeled) as to whether or not they include one or more artifacts and, if an image does include at least one artifact, classified (for example, labeled) as to which type of artifact(s) exists in the image. The stages of the machine learning model may be trained with a number of previously labeled images to improve capabilities of identifying artifacts in the images. Further details regarding the machine learning model are provided below with respect to FIGS. 2A-3C.

The image(s) 112 generated by the aberrometer 104 and/or cameras of the system 100 are displayed to the operator during the procedure. In some embodiments, the user interface 108 may display the images 112 for viewing and/or manipulating by the operator. In some instances, the user interface 108 may also present the operator with information regarding the images 112 after analysis and processing by the controller 106 using the one or more machine learning models.

The user interface 108 may present one or more image quality indicators, such as quality bar graphs, and values for the images displayed on the user interface 108. For example, the user interface 108 may indicate to the operator that a particular image or series of images contains a first artifact (for example, glint) with a probability of 4%, a second artifact (for example, bubbles) with a probability of 94%, a third artifact (for example, debris) with a probability of 1%, and no artifact with a probability of 1%. Thus, the system 100 enables an operator to quickly and meaningfully monitor quality of image data captured by the system 100, which beneficially improves the quality of the procedure being performed and the ultimate patient outcome.

The user interface 108, as provided by the system 100 or a central processing system, can identify when a particular image does or does not include various types of artifact (as above) by reducing the quality value of the image when it does include one or more artifacts. The operator may use the quality bar graph or the quality values and corresponding information to determine whether to exclude the image from processing for measurements, etc., and provide such a determination of whether to exclude the image from processing to the controller of the system 100 or the central processing system. In some embodiments, the controller 106 may automatically determine when to exclude the image from processing for measurements based on the quality values. For example, when the displayed image also indicates a high probability that it contains at least one artifact, the operator or the automatic processing by the controller 106 may determine that the image should be excluded from measurement generation based thereon. On the other hand, when the displayed image indicates a low probability of containing any artifacts, then the operator and/or the automatic processing by the controller 106 may determine that measurements should be generated based on the image. Further details regarding the quality bar graphs and values are provided below.

Thus, system 100 may be used in the surgical procedure to capture the images 112 of the patient's eye 110 and to assess the quality of the image 112 via machine learning models and determine whether the image 112 includes one or more artifacts.

Note that while various aspects described herein are discussed with respect to ocular or similar surgeries and procedures as an example, the techniques described herein can be applied in other medical imaging contexts, such as x-ray images, magnetic resonance imaging (MM) scans, computerized tomography (CT) scans, and the like.

Example Data Flow for Classifying Images During a Medical Procedure

FIG. 2A depicts a data flow 200 for processing an individual input image 202 with a machine learning model 203 implemented by the system 100 of FIG. 1.

In brief, the data flow 200 comprises receipt of the image 112 from the aberrometer 104. The image 112 may be preprocessed by preprocessing module 201 to generate an input image 202 for processing by the machine learning model 203. In this example, machine learning model 203 includes two stages: a first stage 204 that generates a feature vector 206 and a second stage 208, which generates at least one output vector, for example, representing one or more artifact probabilities 210, 212, and 214 that the input image 202 includes corresponding artifact types. The machine learning model 203 may process each input image 202 to classify whether the input image 202, and, thus, the corresponding image 112, includes one or more artifacts or no artifacts.

In some embodiments, the data flow 200 may occur in or be performed by the controller 106 of FIG. 1 or a similar processing component. In some embodiments, the data flow 200 occurs in or is performed by a separate computing system (not shown), which may comprise one or more computing devices. In some instances, the separate computing system may apply machine learning models to images from multiple systems 100. For example, an ophthalmic practice may include multiple systems 100 used during surgical, diagnostic, or other procedures. Each of these systems 100 may communicate with the separate computing system that can apply machine learning models to captured images of patients' eyes for each of the systems 100. In some embodiments, the separate computing system can be distributed locally, may be cloud-based, or can be a combination thereof.

In some instances, the artifact probabilities 210, 212, and 214 generated by the machine learning model 203 or similar machine learning models may indicate probabilities that the image 112 processed according to the data flow 200 includes one or more artifacts.

In some instances, the preprocessing module 201 is configured to preprocess the image 112 for processing by the machine learning model 203. Specifically, the preprocessing module 201 may receive the image 112 and identify a region of interest in the image 112 and/or convert one or more aspects of the image 112 in preparing the input image 202. The region of interest may be generated based on identification of a particular geographic region such as the center region of the image 112. In some embodiments, the preprocessing module 201 may use intelligence for identifying the region of interest (for example, one or more aspects of image analysis). Furthermore, the preprocessing module 201 may scale the image 112 and/or convert pixel formats, for example converting a pixel format of the image 112 (as generated by the aberrometer 104) to a format compatible with the machine learning model 203. Furthermore, the preprocessing module 201 may adjust a number of channels of the image 112.

The image 112 may be captured by one of the cameras introduced above (for example, based on the information from the aberrometer 104). The image 112 may be captured having a first color profile and/or size. For example, the image 112 may be a color image having a size of 640×480 pixels. When the image is the color image, the image 112 may comprise three channels of data, such as a red channel, a green channel, and a blue channel, each with corresponding color data. Accordingly, the preprocessing module 201 may preprocess the image 112 to resize the image 112 and ensure that the image 112 includes an expected number of channels. For example, the machine learning model 203 may have an input image parameter size (height (H) in pixels× width (W) in pixels×number of channels (C)) 480×480 pixels by 3 channels (for example, the red channel, the green channel, and the blue channel for the color image).

Thus, for the image 112 that is a color image having the size of 640×480 pixels, the preprocessing module 201 may resize the image 112 to a size of 480×480 pixels (for example, by cropping a center region of interest) and maintain the color channels to generate the input image 202 as a color image with a size of 480×480 pixels. Alternatively, the machine learning model 203 may have an input parameter pixel size of any other values and channel requirement, as established by the first stage 204 discussed in further detail below. In some instances, the color image may include different numbers of channels for different color components in a color model or color space for the color image. For example, color images may utilize one or more of a cyan, magenta, yellow, black (CMYK) color model or a luma/ chroma component color space (for example, Y-Cb-Cr), among others, which may change a number of channels used for corresponding images.

When the image 112 is a grayscale image (as shown), the image 112 may include only a single channel of data. Thus, the preprocessing module 201 may replicate the single channel of data across three channels (for example, instead of the red, green, and blue channels). Such replication of the single channel may comprise band replicating the single channel to create the three channels. Furthermore, the preprocessing module 201 may resize the image 112 as needed, as discussed above. Thus, regardless of the size and number of channels of the image 112, the preprocessing module 201 may process the image 112 to generate the input image 202 in the format expected by the machine learning model 203. In some aspects, the first stage 204 of the machine learning model 203 does not need multiple channels or may need more than three channels. In such cases, the preprocessing module 201 may process the image 112 to create or truncate the number of channels as appropriate for the first stage 204.

The machine learning model 203 may determine whether each input image 202 processed by the machine learning model 203 includes any artifacts. For example, the machine learning model 203 may determine whether the input image 202 of the interferogram type includes one or more artifacts caused by one or more of the illumination glint, floating debris (in the patient's eye 110), bubbles (in the patient's eye 110), or another distortion, introduced above. The machine learning model 203 may generate one or more output vectors that represent one or more probabilities that the processed image includes one or more artifacts of one or more artifact types. In embodiments where the machine learning model 203 is capable of determining whether the input image 202 includes multiple artifacts, the machine learning model 203 may generate an individual output vector for each artifact. For example, the machine learning model 203 may generate the output vector to include the artifact probability 210 indicating the probability that the input image 202 includes at least one glint artifact, the artifact probability 212 indicating the probability that the input image 202 includes at least one debris artifact, and the artifact probability 214 indicating the probability that the input image 202 includes at least one bubble artifact. More specifically, in certain embodiments, the machine learning model 203 may output a single length-3 vector (i.e., having three elements). The three elements of the output vector may correspond to the three artifact probabilities (for example, the artifact probability 210, the artifact probability 212, and the artifact probability 214, as introduced above). Each element of the output vector, thus, may classify the image as containing 0 or at least one incidence of the corresponding artifact based on the corresponding probability values.

As introduced above, the machine learning model 203 may comprise the first stage 204, which generates the feature vector 206 based on the input image 202, and a second stage 208, which generates the artifact probabilities 210, 212, and 214. The first stage 204 may comprise a feature extraction stage and may be configured to generate a representation of the input image 202. For example, the feature vector generated by the first stage 204 may represent one or more characteristics of the input image 202. In image processing as described herein, the features may correspond to various aspects of the image and pixels forming the image.

The second stage 208 of the machine learning model 203 may process the feature vector generated by the first stage 204 to generate the artifact probabilities 210, 212, and 214. The second stage 208 may correspond to or comprise a classification stage. The classification stage may take the feature vector generated by the first stage 204 and identify which artifact(s), if any, the processed image includes.

In an example use case, the system 100 may capture the image 112 having an image size of 640×480 pixels and having a single channel (for example, because it is a grayscale image). The image 112 may include one or more bubble artifacts. The controller 106 (or other processing component) may employ the preprocessing module 201 to crop the image 112 to have a second image size of 480×480 pixels and replicate the single channel image 112 across three channels to create the input image 202. The controller 106 may then process the cropped and replicated input image 202 with the machine learning model 203 to generate the artifact probabilities 210, 212, and 214. In the captured image 112 having the one or more bubble artifacts, the machine learning model 203 may generate the artifact probability 210 indicating that the image 112 has a probability of 1% of including a glint artifact, generate the artifact probability 212 indicating that the image 112 has a probability of 24% of including a floater artifact, and generate the artifact probability 214 indicating that the image 112 has a probability of 75% of including a bubble artifact. Thus, the artifact probabilities indicate that the image 112 has a low probability of including glint and floater artifacts (0.01 and 0.24, respectively) and a high probability of including a bubble artifact (0.75).

In some instances, the processing component may use the artifact probabilities generated by the machine learning model 203 to generate the quality bar graph or quality values introduced above, for example via the user interface. For example, based on the artifact probabilities 210, 212, and 214 identified above, the processing component may generate the quality values for display to the operator. For example, the processing components may generate the quality bar graph and/or values based on Eq. 1, where the artifact_n_probability is the probability generated in the output vector generated by the second stage 208 for the corresponding artifact type:

$$\text{Quality Value} = 1.0 - \text{artifact\_}n\text{\_probability} \qquad (\text{Eq. 1})$$

Thus, for the example above where the artifact probabilities 210, 212, and 214 indicate that image 112 indicates a probability of 0.01 that the image 112 includes a glint artifact, a probability of 0.24 that the image 112 includes a floater artifact, and a probability of 0.75 that the image 112 includes a bubble artifact, the quality bar graph, quality values, or other indicators for the image 112 may be converted to a percentage:

For the glint artifact, 1.0−0.01=0.99, or 99%;
For the floater artifact, 1.0−0.24=0.76, or 76%; and
For the bubble artifact, 1.0−0.75=0.25, or 25%.

In some instances, the controller 106 generates the quality information for display for the output vectors generated by the machine learning model 203 (i.e., for the artifact probabilities represented by the output vectors). Alternatively, or additionally, the controller 106 may generate quality information for display based on comparison of these values to a threshold. For example, the controller 106 may only generate quality value data for operator review when the quality of the image 112 is below a threshold or above the threshold, such as 50% (making the quality value less than 0.5 and the probability greater than 0.5). In some embodiments, the threshold for generating the quality value data may fall in a range of 25-50% (for example, 25%, 30%, 40%, 45% or 50%, or any value therebetween) or in a range of 50%-75% (for example, 50%, 55%, 60%, 65%, 70%, or 75%, or any value therebetween). The threshold also may be established and/or adjusted based on one or more of historical data (for example, variable based on observed trends), selectable by an operator, or the like. Additionally, or alternatively, the threshold may be established by the operator or facility. In some embodiments, the controller 106 generates quality value data for operator review for all images but applies labels for display with the images based on one or more threshold ranges.

Figure 8A:
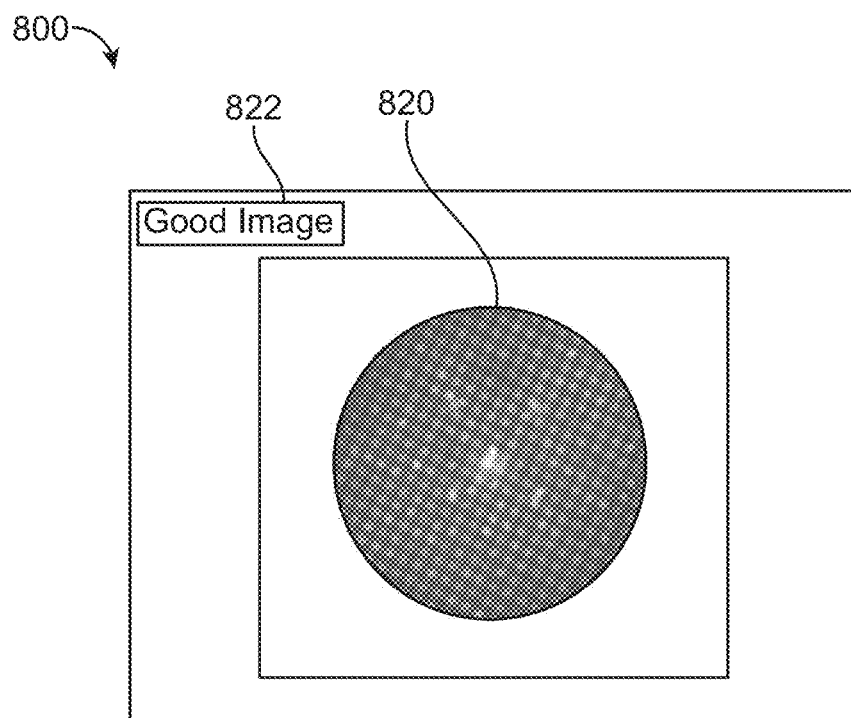
FIGS. 8A-8O are display concepts for providing digital images of the patient's eye to a user with details of any detected artifacts via a graphical user interface, in accordance with certain embodiments.
Figure 8B:
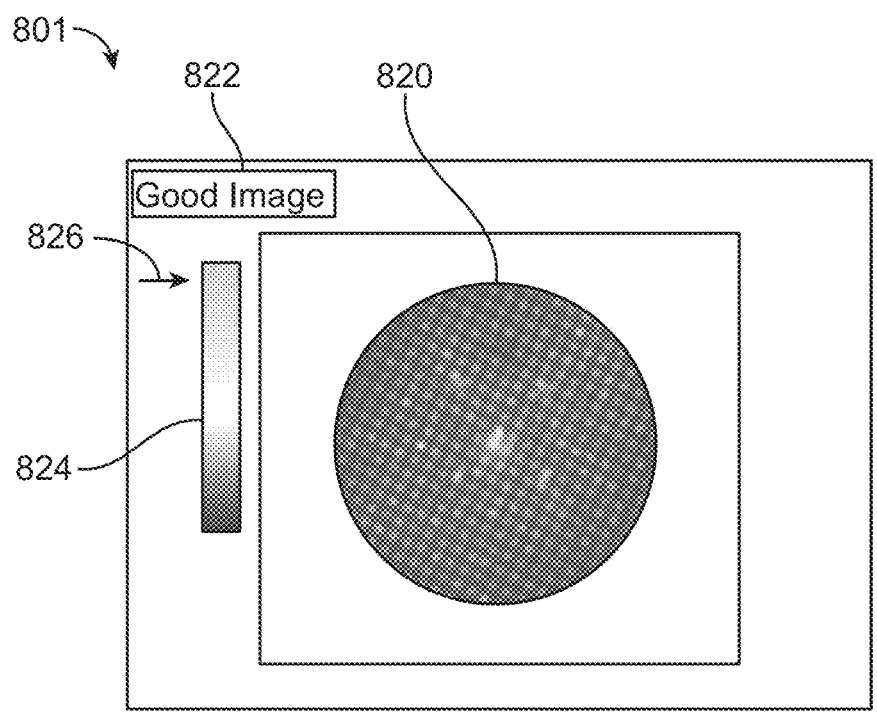
Figure 8C:
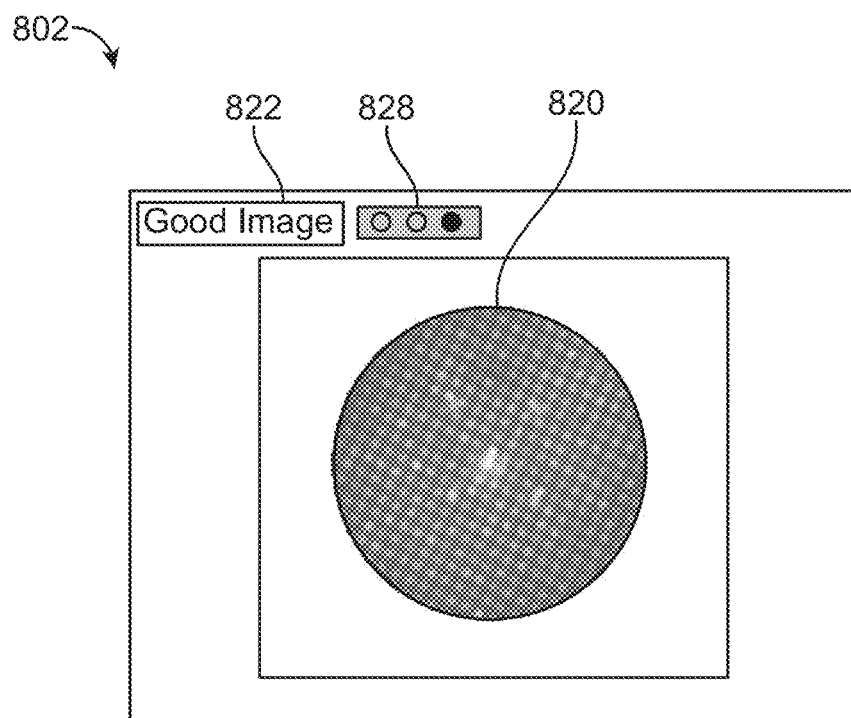
Figure 8D:
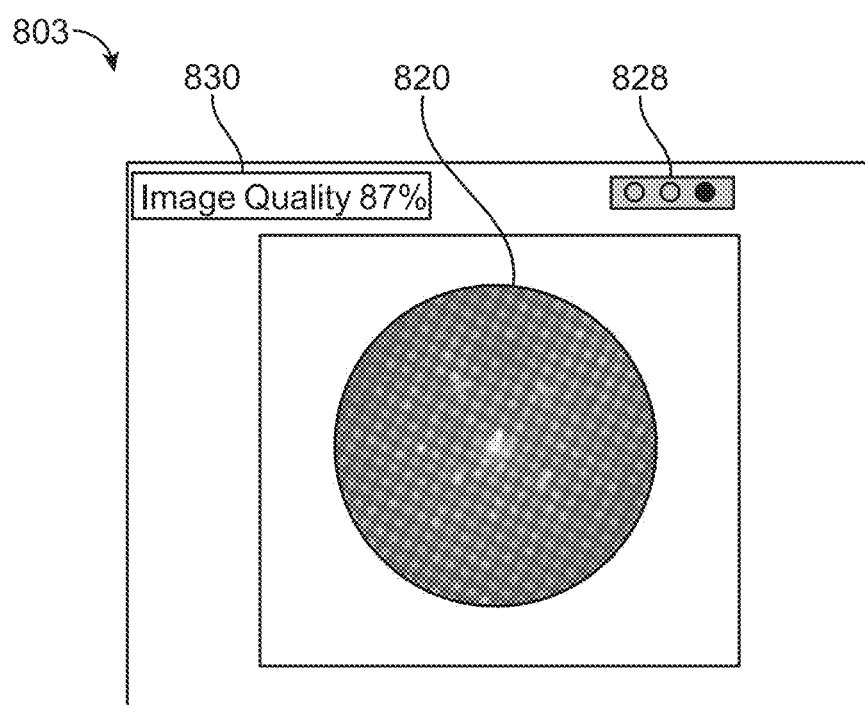
Figure 8E:
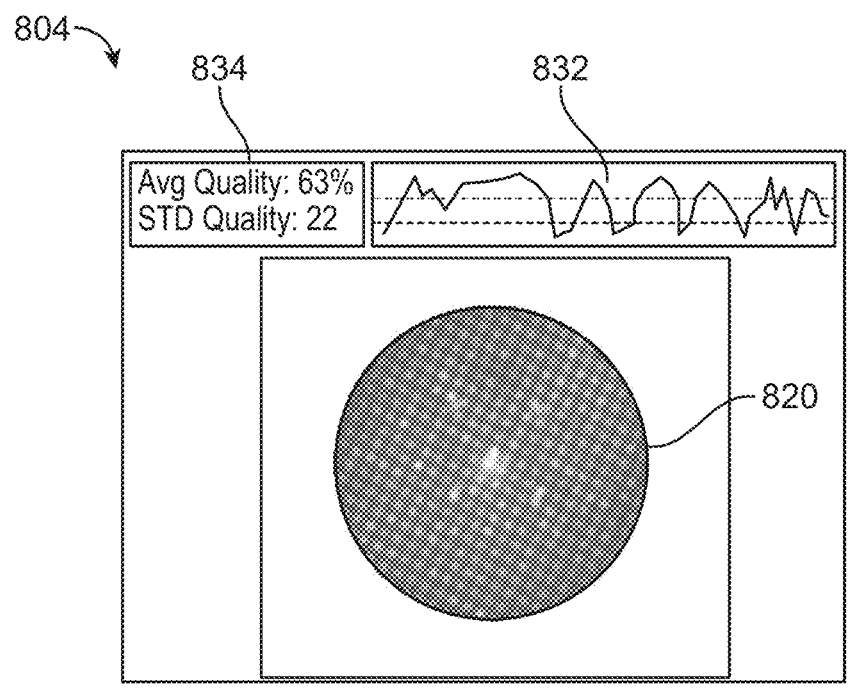
Figure 8F:
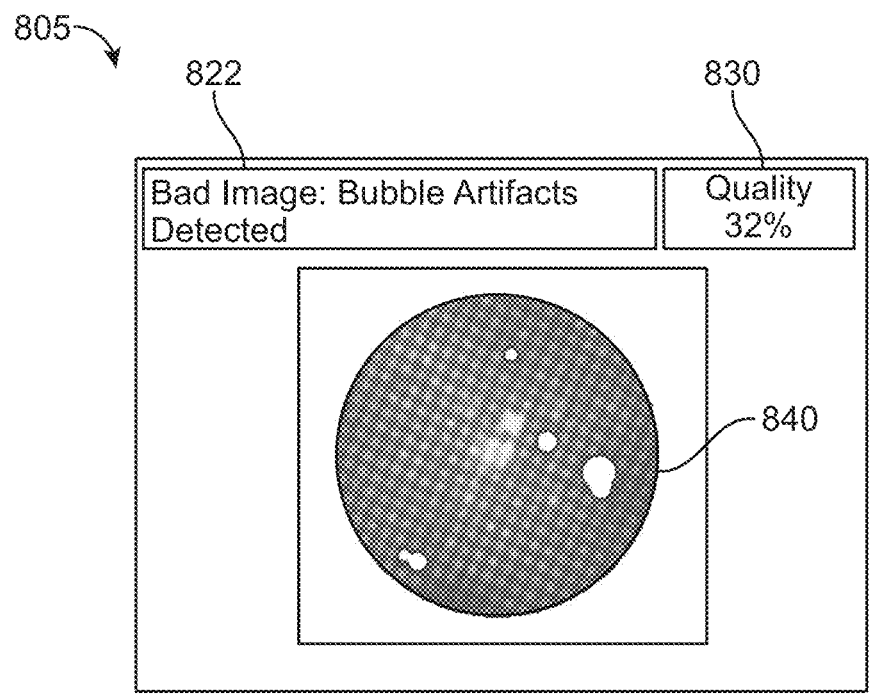
Figure 8G:
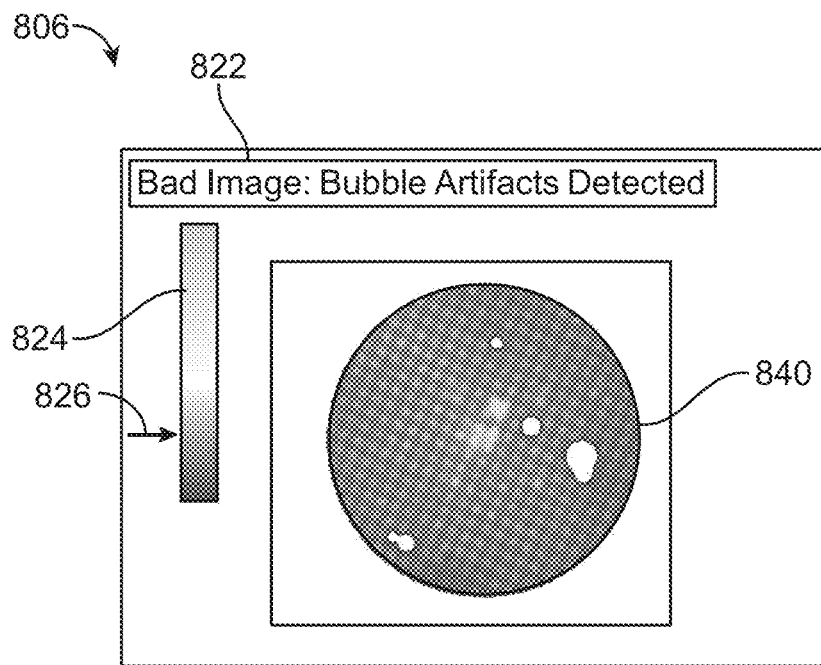
Figure 8H:
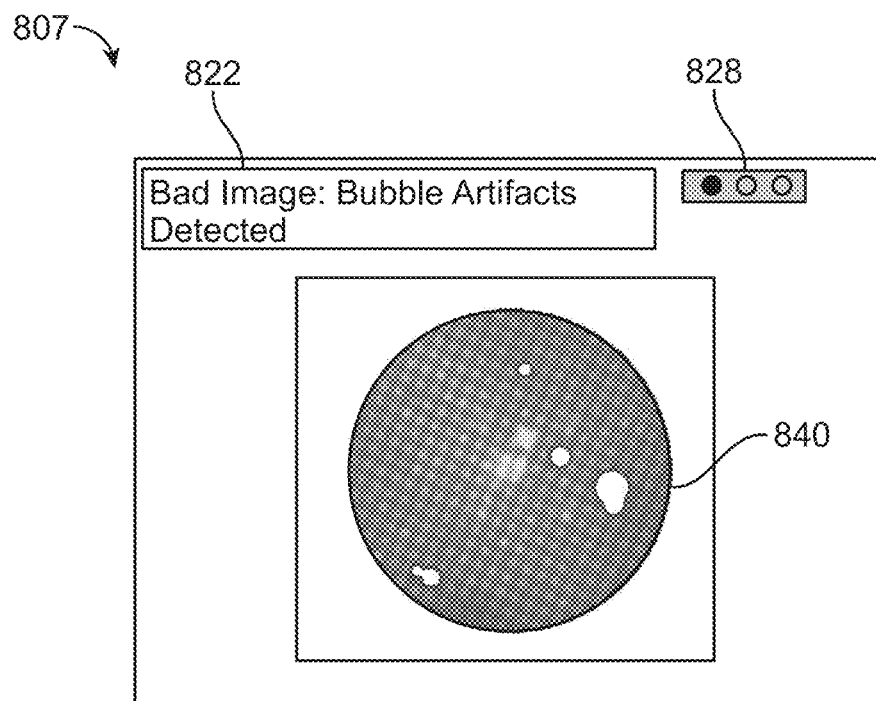
Figure 8I:
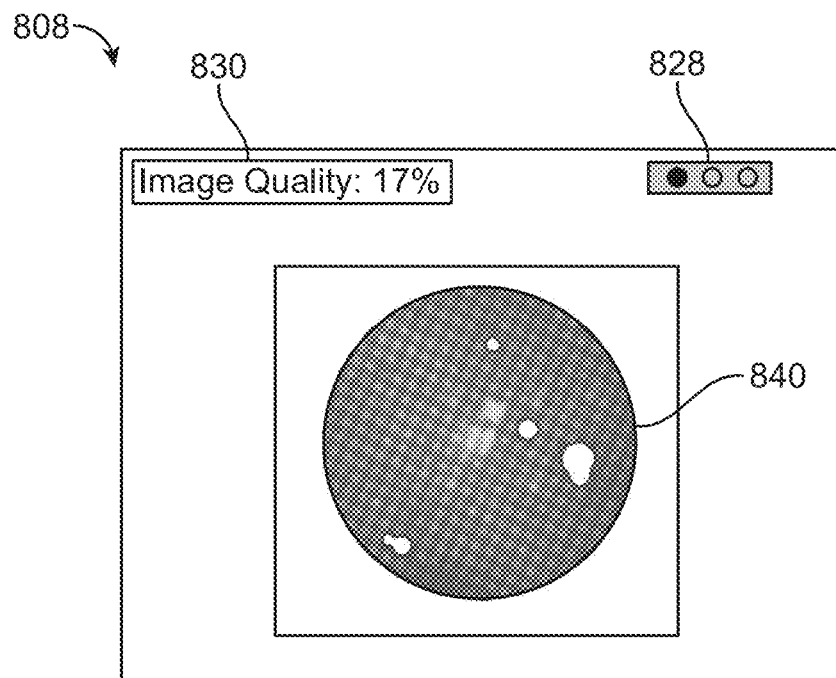
Figure 8J:
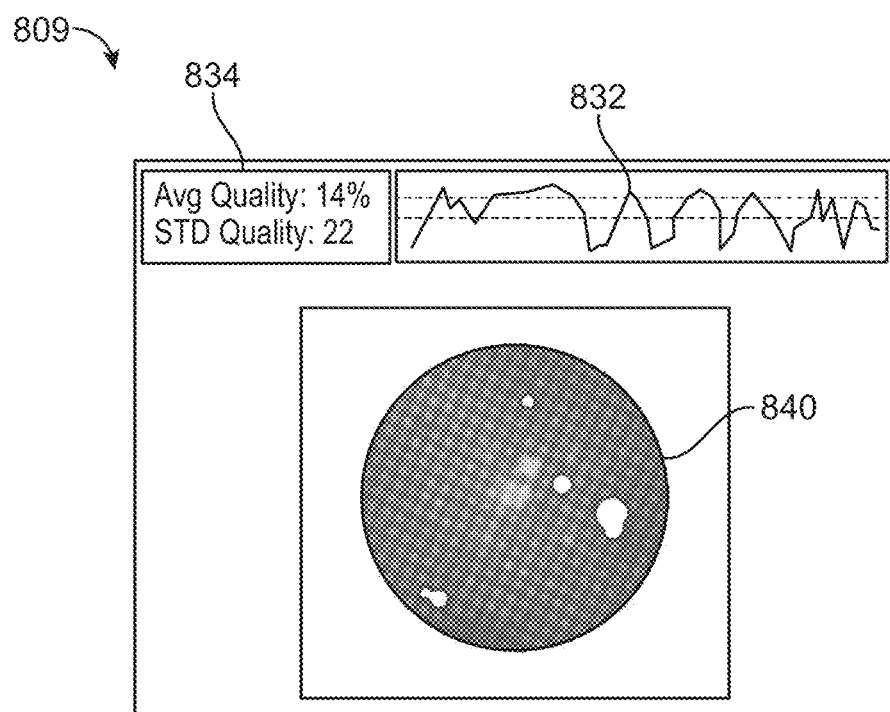
Figure 8K:
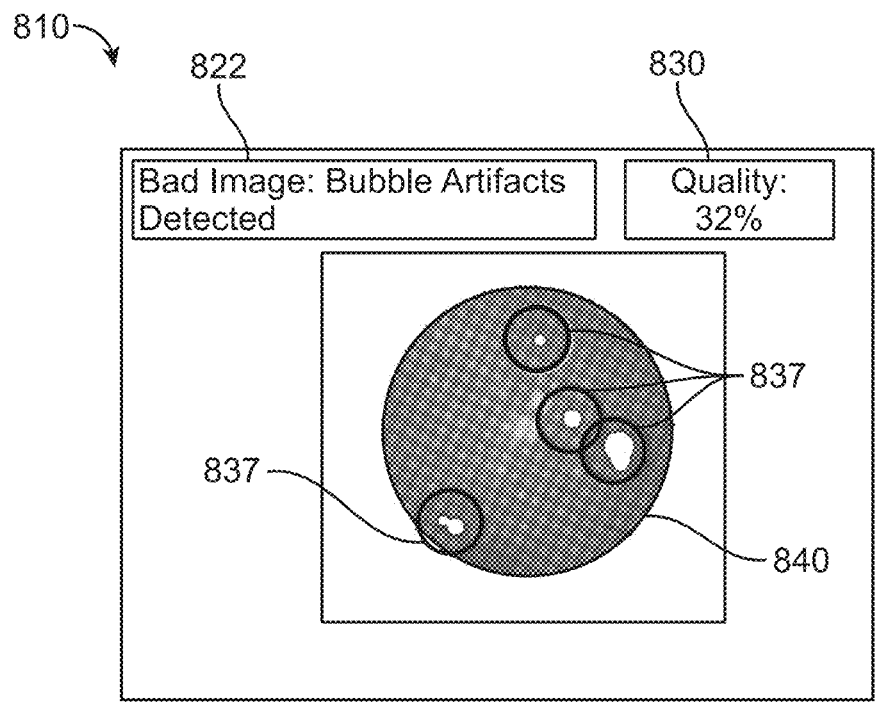
Figure 8L:
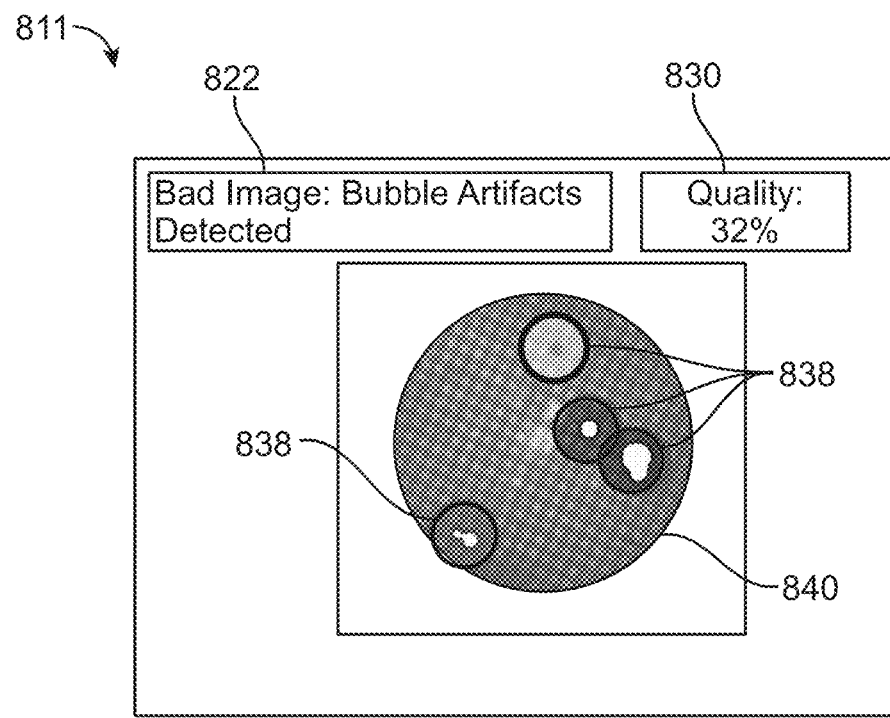
Figure 8M:
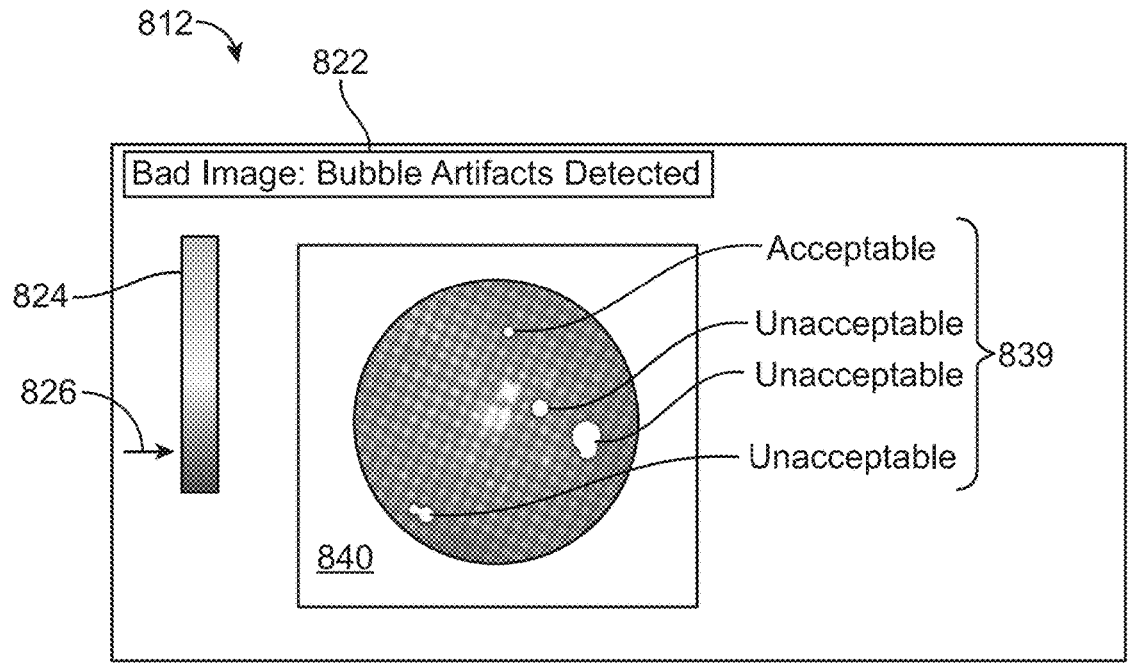
Figure 8N:
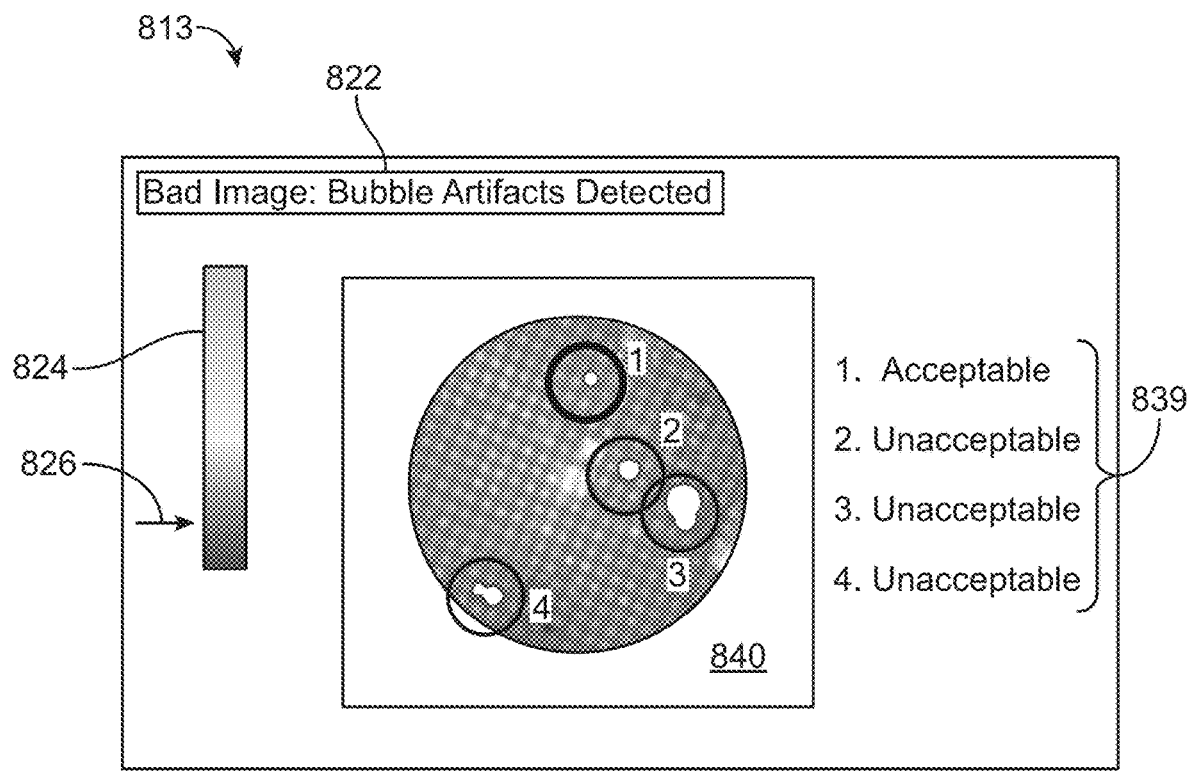
Figure 8O:
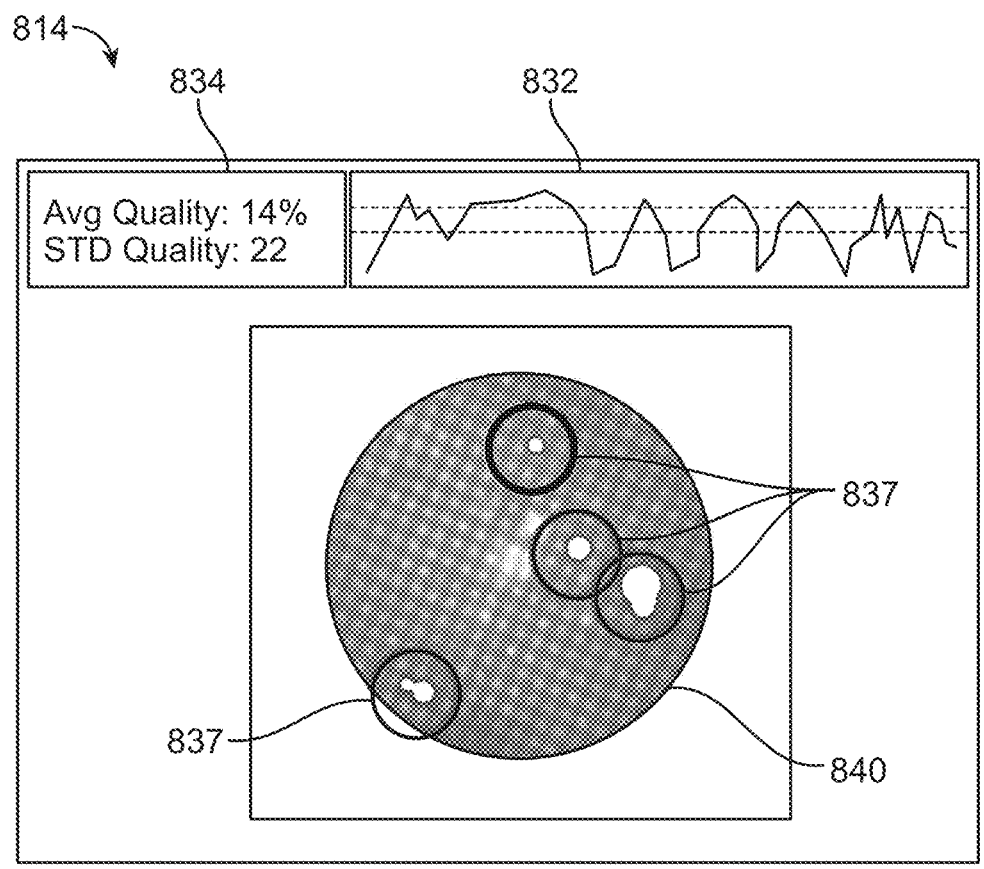

Such threshold ranges may also be used to determine one or more labels (for example, "Good", "Bad", "Marginal", and the like) for the images 112, with reference to FIGS. 8A-8O. As such, each image may be displayed or associated with a label based on different ranges of image quality values. For example, an image quality of 0%-50% may correspond to a "Bad Image" label, 51-70% a "Marginal Image" label, and 71-100% a "Good Image" label, or 0%-65% a "Bad Image" label, 66-85% a "Marginal Image" label, and 86-100% a "Good Image" label, and so forth.

Thus, the controller 106 may limit review by the operator to only images 112 that meet a threshold quality level (i.e., are more likely than not to include one or more artifacts). In some embodiments, the controller 106 may provide simplified or generic warnings or prompts to the operator that the quality level threshold was not met by one or more images and provide the operator with options to view more details regarding individual images that did not meet the threshold quality level and/or corresponding artifact(s) that caused the threshold quality level to not be met.

Similarly, the controller 106 may prompt the operator whether the images 112 should be used to generate measurement data. In some instances, the controller 106 will provide a recommendation to the operator to limit further processing of the images 112 to prevent or exclude processing of the images 112 having quality values that fall below the threshold quality level from being used to generate measurement data. Alternatively, the controller 106 will automatically exclude processing of the images 112 into measurement data without operator input based on the quality values for the images 112. Furthermore, the controller 106 may provide the operator with one or more recommendations to remedy the artifact causing the quality threshold level for an image to not be met. For example, the controller may instruct the operator to reposition one or more of the cameras, cleaning equipment, and the like.

Furthermore, as introduced above, the controller 106 may generate the user interface 108 to identify locations of any artifacts in the image 112. In some instances, the controller 106 may implement an additional machine learning model (not shown) to identify the locations of the artifacts included in the image 112. By identifying the locations of the artifacts in the image 112 on the user interface 108, the controller 106 enables the operator to more easily and quickly make a determination whether or not to use the image 112 to generate intraoperative measurement data.

In some embodiments, when the controller 106 identifies that quality for the image 112 is below the desired threshold (i.e., determines that the image 112 includes one or more artifacts that reduce the quality of the image below the threshold), the controller 106 may display a message indicating to the operator that the image 112 was not used to generate measurements because the quality is too low. Such determinations may be made automatically, as described herein, and without operator input. Alternatively, or additionally, when the controller 106 determines that the quality for the image 112 is sufficiently high, then the controller 106 may permit processing of the image 112 for measurement generation and provide those measurements with the image 112 and quality values to the operator via the user interface, in real-time during the procedure.

The machine learning model 203 described above may process images of a first type, for example, the interferogram type. While aspects of the machine learning model 203 may be generic to any image type (for example, the first, or feature extraction, stage 204), because the different image types may include different artifacts having different characteristics when captured in the image 112, the second, or classification, stage 208 may employ different designs or architectures for the different image types (e.g., different layer configurations). Thus, multiple or different combinations of the feature extraction stage (i.e., the first stage 204) and different classification stages (i.e., the second stage 208 and additional stages) for machine learning models may be used to determine whether the images 112 of different types include different types of artifacts, as described further with respect to FIG. 2B below.

Example Data Flows for Classifying Images During a Medical Procedure Using Machine Learning Models FIG. 2B depicts a set of data flows 250a-250c for processing multiple images 112a, 112b, and 112c with different machine learning models 203, 217, and 227, respectively. Each of the machine learning models 217 and 227 has a similar structure as the machine learning model 203 of FIG. 2A. The separate data flows 250a-250c may indicate parallel processing and/or multi-model capabilities for the system 100.

As described above, the aberrometer 104 may provide the images having different image types, such as from different image sensors in aberrometer 104 creating image data simultaneously. For example, the images 112a, 112b, and 112c may be one of the wide field type, the focus view type, and the interferogram view type. Each image type includes different kinds of artifacts. Thus, each image 112a, 112b, and 112c may be processed by a different machine learning model 203, 217, and 227.

For example, the machine learning model 203 of FIG. 2B may identify glint, debris, and/or bubbles in the interferogram view type image 112a. The machine learning model 217 may identify debris (for example, debris on the combiner mirror or beam-splitter introduced above) in the image 112b of the wide field view type. The machine learning model 227 may identify changes in fluid in the patient's eye 110 (for example, excess drying or excess fluid in one or more portions of the patient's eye 110) in the image 112c of the focus view type. Further details regarding the machine learning models 217 and 227 of FIG. 2B are provided below.

The data flow 250a corresponds to the data flow 200 of FIG. 2A, with the exception that the image 112 that feeds the preprocessing module 201 is identified as image 112a. The remaining components of the data flow 250a correspond to the components of the data flow 200 in FIG. 2A. As described above with reference to FIG. 2A, the second stage 208 may take the features vector 206a generated by the first stage 204 and identify which artifact(s), if any, the processed image 112a of the interferometer type includes.

The data flow 250b includes components similar to the data flow 250a, with similarly numbered components having characteristics as described with reference to FIG. 2A. The data flow 250b includes the image 112b that is preprocessed by the preprocessing module 201 to generate an input image 202b. The preprocessing module 201 may preprocess the image 112b to generate the input image 202b as described above with respect to the preprocessing module 201 of FIG. 2A. The input image 202b is processed by the machine learning model 217 to generate one or more artifact probabilities, for example, one or more of artifact probabilities 220, 222, and 224. The machine learning model 217 includes the first stage 204 (i.e., the feature extraction stage) that generates the features vector 206b based on the input image 202b, similar to the first stage 204 generating the feature vector 206 as introduced above with respect to FIG. 2A.

The features vector 206b generated by the first stage 204 is processed by a second stage 218 (i.e., a classification stage different than the second stage 208) to generate one or more of the artifact probabilities 220, 222, and 224. The second stage 218 of the machine learning model 217 may process the features vector 206b generated by the first stage 204 to generate one or more of the artifact probabilities 220, 222, and 224. The second stage 218 may correspond to or comprise the classification stage, similar to the classification stage of the second stage 208, but trained to classify and/or identify different artifact types than the second stage 208. As described above with reference to FIG. 2A, the second stage 218 may take the features vector 206b generated by the first stage 204 and identify which artifact(s), if any, the processed image of the wide field type includes.

The second stage 218 may start as the same architecture, parameters, weights, etc., as the second stage 208 but be trained independently and, thus, evolve to fit its input data specific features. For example, the second stage 208 can be trained to generate one or more of artifact probabilities 210, 212, and 214 for the interferogram image type while the second stage 218 can be trained to generate one or more of artifact probabilities 220, 222, and 224 for the wide view type images 112b.

The data flow 250c includes components similar to the data flow 250a. Specifically, the data flow 250c includes the image 112c that is preprocessed by the preprocessing module 201 to generate an input image 202c. The preprocessing module 201 may preprocess the image 112c to generate the input image 202c as described above with respect to the preprocessing module 201 of FIG. 2A. The input image 202c is processed by the machine learning model 227 to generate a corresponding output vector, for example, representing one or more of artifact probabilities 230, 232, and 234. The machine learning model 227 includes the first stage 204 (i.e., the feature extraction stage) that generates the feature vector 206c based on the image 112c, similar to the first stage 204 generating the features vector 206a as introduced above with respect to FIG. 2A.

The features vector 206c generated by the first stage 204 is processed by a second stage 228 (i.e., a classification stage different than the classification stages of the second stage 208 and the second stage 218) to generate one or more of the artifact probabilities 230, 232, and 234. The second stage 228 may correspond to or comprise the classification stage, similar to the classification stage of the second stage 208. As described above with reference to FIG. 2A, the classification stage may take the features vector 206c generated by the first stage 204 and identify which artifact(s), if any, the processed image of the focus view type includes.

The second stage 228 may start as the same architecture, parameters, weights, etc., as the second stage 208 and the second stage 218 but be trained independently and, thus, evolve to fit its input data specific features. For example, the second stage 208 can be trained to generate one or more of artifact probabilities 210, 212, and 214 for the interferogram image type while the second stage 228 can be trained to generate one or more of artifact probabilities 230, 232, and 234 for the focus view type images 112c.

Each of the images 112a, 112b, and 112c, which may be of different image types and which feed into different machine learning models 203, 217, and 227 respectively, may be processed by the same feature extraction stage (i.e., the first stage 204) but different classification stages (i.e., the second stage 208, the second stage 218, and the second stage 228, respectively). The corresponding output vectors then indicate probabilities that each image 112a, image 112b, and image 112c includes one or more artifacts corresponding to the respective image type. For example, the artifact probabilities 210, 212, and 214 indicate the probabilities that the interferogram view type image 112a includes one or more of glint, bubbles, or floaters (respectively), while the artifact probabilities 220, 222, and 224 indicate probabilities that the wide view type image 112b includes one or more of artifacts caused by debris or instrument placement and the artifact probabilities 230, 232, and 234 indicate probabilities that the focus view type image 112c includes one or more artifacts caused by hydration concerns (drying or pooling of tears) or motion.

In some embodiments, though not shown in FIG. 2B, the machine learning models 203, 217, and 227 may be combined or otherwise structured to employ a single, common first stage 204 that generates features vectors 206a, 206b, or 206c based on the images 112a, 112b, and 112c for processing by the three second stages 208, 218, and 228. For example, the first stage 204 may receive all the input images 202a, 202b, and 202c as generated by the preprocessing module 201. The first stage 204 may generate the features vector 206a based on the input image 202a, the features vector 206b based on the input image 202b, and the features vector 206c based on the input image 202c. Thus, the first stage 204 may then feed the corresponding features vectors 206a, 206b, and 206c to the corresponding second stage 208, 218, and 228, respectively. Such an architecture may reduce overhead and resource consumption at a cost of requiring additional time for processing.

Figure 3A:
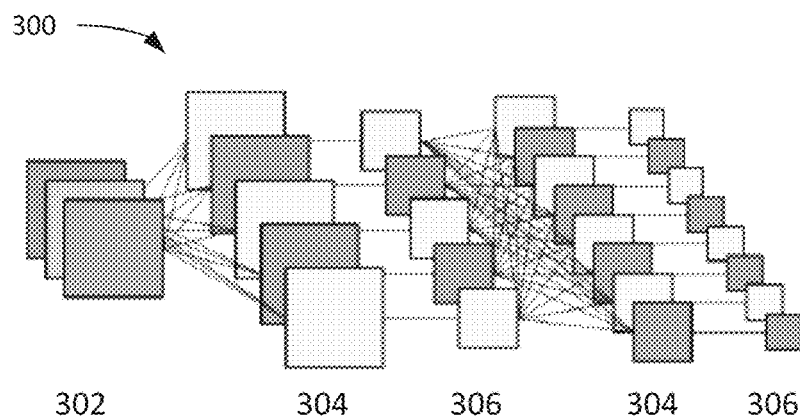
FIG. 3A depicts an architecture for a convolutional neural network (CNN) applied as a feature extraction stage of the machine learning model implemented by the system of FIG. 1, in accordance with certain embodiments.

Example Architectures of Stages for the Image Classification Machine Learning Model In some embodiments, the feature extraction stage of the machine learning model 203 can comprise a feature generating deep neural network, for example, the feature extraction portions of a convolutional neural network (CNN), a multi-layer perceptron neural network (MLP), or similar neural network. FIG. 3A depicts an example architecture for the CNN applied as the feature extraction stage that generates the feature vector 206 for individual images 112 provided by the camera(s) and processed and/or analyzed by the CNN. The CNN may be different from other neural networks and deep neural networks because the CNN may apply convolutions as opposed to matrix multiplication in layers of the CNN.

As shown in FIG. 3A, the CNN 300 comprises a multi-layer neural network configured to process input images. The CNN 300 includes a plurality of neurons divided into a combination of an input layer 302, convolution layer(s) 304 (which may comprise hidden layers), and pooling layers 306. One of the convolution layers 304 may be considered a hidden layer when inputs and outputs of the convolution layer 304 are masked. The CNN 300 applied herein as the first stage 204 may have its fully connected layers and output layers removed and replaced with layers of the classification stage, as introduced above and described in further detail below. The CNN 300 may be applied by the controller 106 or a specialized processor and may be representative of a neural network used to implement each of the feature extraction stage of one or more of machine learning models, for example the machine learning models 203, 217, and 227 described above with reference to FIGS. 2A and 2B.

Specifically, the architecture for the CNN 300 includes the input layer 302 comprising three channels. For a color image, each channel of the input layer 302 corresponds to a different color of red, green, and blue. The input layer 302 may receive an input comprising a number of images each having a height, width, and the number of channels. The CNN 300 may be configured to handle any value for any of these aspects of the CNN 300. For the image processing and classification examples described herein, the feature extraction stage may comprise the CNN 300 having an architecture with a number of input images, each having a size of approximately 480×480 pixels and three channels, although processing of a different number of images each having a different size and/or number of channels is contemplated as well.

The architecture for the CNN 300 further includes a number of convolution layers 304. Each convolution layer 304 may receive an input corresponding to a number of images, image size (height and width) and number of channels for each image. The convolution layer 304 may abstract the image by convolving the input of the convolution layer to generate an output, which is passed to a subsequent layer (for example, another convolution layer 304 or one of the pooling layers 306). The convolution layer 304 may apply a convolution filter on the input. The filter may have a certain size that is applied horizontally and/or vertically along the image being processed with a particular stride that generates an output value for the portions of the image covered by the filter. The controller 106 or the specialized processor may apply the filter to each input image with the corresponding stride to generate the output passed to the subsequent layer. In some embodiments, the convolution filter has a depth that corresponds to a depth of the number of channels of the input layer 302.

As shown in FIG. 3A, the convolution layers 304 are each followed by pooling layers 306. The pooling layers 306 may streamline processing by the controller 106 or specialized processor applying the first stage 204 of the machine learning model 203. Specifically, each pooling layer 306 may reduce dimensions of the output generated by a preceding convolution layer 304. Effectively, the pooling layer 306 may reduce a number of outputs generated by a previous convolution layer 304. The pooling layer 306 may apply one or more of a number of functions to pool the outputs from the previous convolution layer 304. For example, the processing component performing the processing of the machine learning model 203 may apply, for the pooling layer 306, one or more of maximum pooling (which takes a maximum value of a cluster of output portions from the preceding convolution layer 304), an average pooling (which takes an average value of the cluster of output portions from the preceding convolution layer 304), or another pooling calculation. The results of the pooling layer 306 may be provided to a subsequent convolution layer 304 or to an average pooling layer to generate the feature vector to provide to the subsequent stage of the machine learning model 203.

The feature extraction stage may include any number of convolution layers 304 and pooling layers 306, depending on the processing being performed. In some instances, the CNN applied is a VGG16 CNN. The VGG16 CNN may utilize a combination of convolution layers and pooling layers in an arrangement as shown below with respect to FIG. 3B.

Figure 3B:
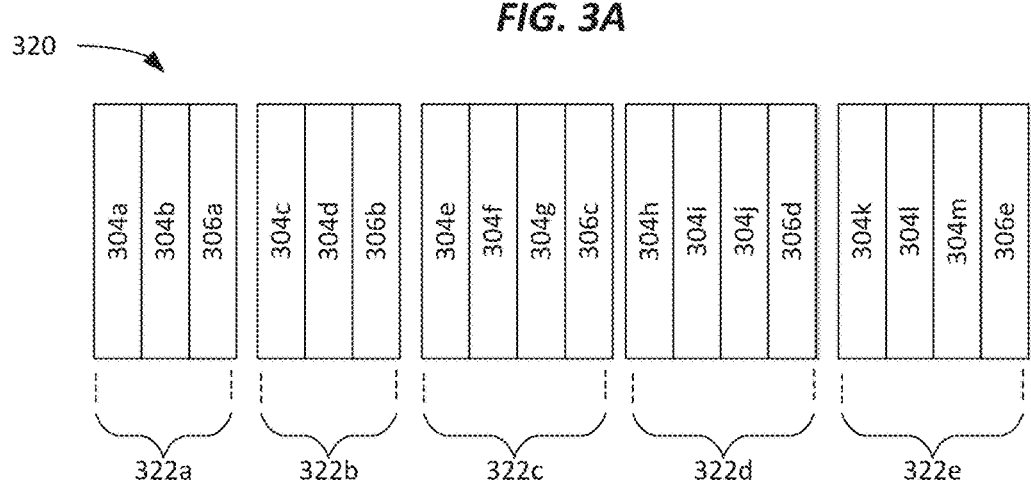
FIG. 3B depicts a representative view of an architecture of the CNN applied for the first stage (i.e., the feature extraction stage) of the machine learning model of FIGS. 2A and 2B, in accordance with certain embodiments.

FIG. 3B depicts a representative view of an architecture 320 of the CNN applied for the feature extraction stage of the machine learning model, for example the machine learning models 203, 217, and/or 227 of FIGS. 2A and 2B. In some embodiments, the architecture 320 applied by the controller 106 or the specialized processor may be representative of a neural network used to implement the feature extraction stage of the machine learning model.

As introduced above, the feature extraction stage may comprise the feature extraction stages of a VGG16 CNN, as shown in FIG. 3B. In the VGG16 CNN architecture 320 shown in FIG. 3B, the architecture 320 includes an input layer 302 and five groupings 322 of convolution layers 304 and pooling layers 306, each grouping including a number of convolution layers 304 and one pooling layer 306. The first grouping 322a includes a first convolution layer 304a, a second convolution layer 304b, and a first pooling layer 306a. The second grouping 322b includes a third convolution layer 304c, a fourth convolution layer 304d, and a second pooling layer 306b. The third grouping 322c includes a fifth convolution layer 304e, a sixth convolution layer 304f, a seventh convolution layer 304g, and a third pooling layer 306c. The fourth grouping 322d includes an eighth convolution layer 304h, a ninth convolution layer 304i, a tenth convolution layer 304j, and a fourth pooling layer 306d. The fifth grouping 322e includes an eleventh convolution layer 304k, a twelfth convolution layer 304l, a thirteenth convolution layer 304m, and a fifth pooling layer 306e. Following the fifth pooling layer 306e, the architecture 320 may include a maximum pooling layer (not shown) that generates the feature vector for the image processed by the VGG16 CNN.

While the architecture 320 represents the VGG16 architecture, it will be understood that the architecture applied for the feature extraction stage may comprise any combination of input layer 302, convolution layers 304, pooling layers 306 and/or additional layers as appropriate to efficiently and accurately generate the feature vector for the input image processed by the architecture 320. These layers may be arranged in various arrangements, numbers, and/or combinations thereof or according to different architectures of different CNNs or deep neural networks (DNNs).

As introduced above, the CNN employed for the feature extraction stage of the machine learning model may not include fully connected layers. Instead, the machine learning model 203 includes the fully connected layers in the classification model (i.e., the second stage 208), described below with respect to FIG. 3C.

Figure 3C:
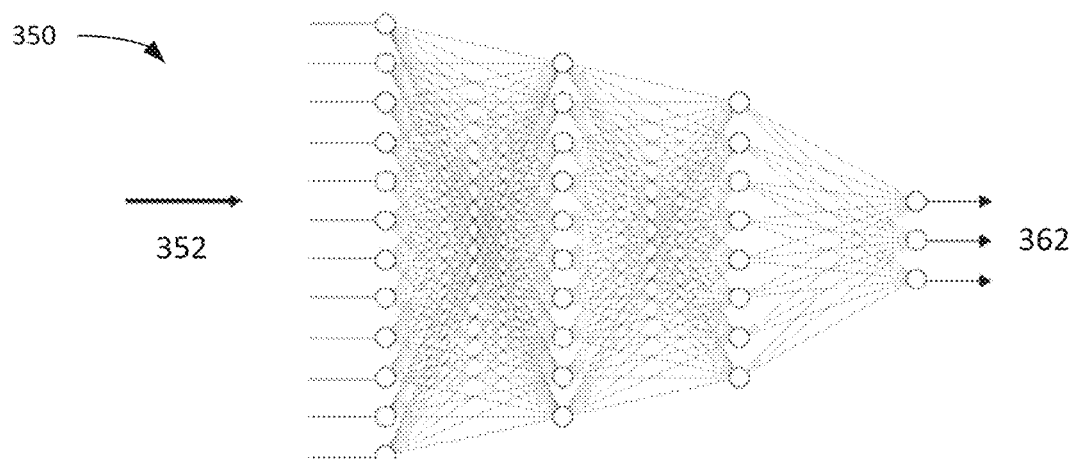
FIG. 3C depicts an architecture of the second stage (i.e., the classification stage) of the machine learning model of the system of FIG. 1 that generates an output vector based on the feature vector generated by the first stage for individual images of the captured digital images, in accordance with certain embodiments.

FIG. 3C depicts an example neural network architecture 350 of the classification model (i.e., the second stage 208) of the machine learning model 203 of the system 100 of FIG. 1 that generates an output vector based on the feature vector generated by first stage 204 for individual images of the captured digital images. The neural network architecture 350 shows a multi-layer deep neural network according to an example embodiment. In some embodiments, the neural network architecture 350 applied by the processing component (i.e., the controller 106 or a specialized processor) may be representative of a neural network used to implement one or more of the second stage 208, the second stage 218, or the second stage 228 (i.e., one of the classification stages) of one or more of the machine learning models 203, 217, or 227 described above with reference to FIGS. 2A and 2B.

The neural network architecture 350 may process input data 352 (corresponding to the feature vector output by the feature extraction stage) using an input layer 354. The input data 352 may correspond to the feature vector output by the first stage 204. The input layer 354 includes a plurality of neurons as shown. The neurons may individually condition the input data 352 by scaling, range limiting, and/or the like. Each of the neurons in the input layer 354 generates an output that is fed to inputs of a subsequent hidden layer 356. Each hidden layer 356 comprises a plurality of neurons that process the outputs from the previous layer (for example, either the input layer 354 or another hidden layer 356). In some examples, each of the neurons in one of the hidden layers 356 generates an output that is then propagated through one or more additional hidden layers 356. The neural network architecture 350 may include any number of hidden layers 356. The final hidden layer 356 may include a plurality of neurons that process the outputs from the previous hidden layer 356 to generate outputs fed to an output layer 360. The output layer 360 includes one or more neurons that process the output from the hidden layer 356. It should be understood that the neural network architecture 350 is representative only and that other architectures are possible, for example, architectures including different numbers of hidden layers 356, without one or more of the input layer 354 or the output layer 360, including recurrent layers, and the like.

In some examples, each of the neurons in the various layers of the neural network architecture 350 takes a combination of its inputs (for example, a weighted sum of a trainable weighting matrix W) and adds an optional trainable bias b. In some examples, certain neurons, for example neurons of the output layer 360, may comprise an activation function $f$. The activation function may generally be a non-linear activation function, such as a sigmoid activation function. However, other activation functions are possible, such as an activation function with upper and/or lower limits, a log-sigmoid function, a hyperbolic tangent function, a rectified linear unit function, and/or the like. In some examples, each of the neurons of the output layer 360 may have the same or a different activation function as one or more other neurons of the output layer 360.

In some embodiments, a number of neurons in the input layer of the classification stage is equal to the number of elements in the feature vector generated by the feature extraction stage.

The input layer of the classification stage may apply trained weights to the feature vector received and pass the generated results to the first hidden layer of a plurality of hidden layers. The first hidden layer may include double the neurons of the input layer, with each subsequent hidden layer having half the neurons of the previous hidden layer. The neurons for the hidden layers may comprise Rectified Linear Unit activation functions. Alternatively, the neurons for the hidden layers may comprise one or more other activation functions. The output layer of the classification stage may include a number of neurons equal to a number of artifact types for the type of image being processed and having the sigmoid activation function.

Thus, in one example, the input layer 354 has a number of neurons equal to the length of the feature vector 206, or 512 neurons for the 512 element feature vector generated by the VGG16 CNN introduced above. The input layer 354, after applying the trained weights, generates outputs to the first hidden layer 356, which may have 1024 neurons. Each subsequent hidden layer 356, with neurons having the RELU activation function, will have half the neurons of the previous hidden layer 356, until the output layer 360, which has three output neurons, one each for the artifacts of the interferometer type image (i.e., one neuron for each of glint, floater, and bubble artifacts) and generating the artifact probabilities 362. The artifact probabilities 210, 212, and 214 (for example, for the interferogram view type image 112a), as previously described, may provide probabilities that the image 112 includes each of the corresponding artifact types.

In some embodiments, the system employing the machine learning model (and similar machine learning models) provide various improvements in correctly identifying whether or not images include one or more artifacts. For example, the system can correctly identify a training image that includes one or more artifacts approximately 97% of the time and correctly identified whether or not a testing image included one or more artifacts approximately 91% of the time, an improvement over the existing technologies. More specifically, the system employing the machine learning model correctly identified the training images having glint artifacts 99% of the time and correctly identified whether or not the testing images included the glint artifacts 91% of the time. Additionally, the system employing the machine learning model correctly identified the training images having floater artifacts 97% of the time and correctly identified whether or not the testing images included the floater artifacts 95% of the time. Furthermore, the system employing the machine learning model correctly identified the training images having bubble artifacts 97% of the time and correctly identified whether or not the testing images included the bubble artifacts 97% of the time. Further training (as described below) may improve the artifact detection capabilities of the system over the existing technologies.

Training and Improvement of Machine Learning Models

In some examples, the machine learning model 203 (and the various stages described above) may be trained using one or more learning methods. The machine learning model 203 may be trained using a collection of images that have been labeled with respect to containing one or more artifacts. The images may be images captured from a variety of previous procedures or images of eyes not from other procedures. In some instances, the images are Talbot-Moire interferometer images, and the data set is randomly split into the training, validating, and testing subsets of images, though various other types of images may be classified using the machine learning model 203. Each of the images in the collection may have been manually reviewed and labeled with respect to artifacts contained therein. For example, each image may be labeled to indicate whether or not the image includes one or more bubble regions, one or more floater regions, one or more glint regions, one or more artifacts, and the like.

Those images labeled as having one or more artifacts may include additional label information including what one or more artifacts the image includes. For example, an image of an eye that includes bubbles and debris may have a label indicating that the image includes artifacts and that the artifacts are bubbles and debris. In some instances, the labeled image (and the dataset in general) includes location information for where the one or more artifacts are located and the location information may be associated with the type of artifact included. For example, when the image is labeled as including bubbles and debris, the image may also be labeled to show where the bubbles are located and where the debris is located, such that each location is identified by the type of artifact it includes.

In some embodiments, the feature extraction stage is set to the weights previously trained using the dataset of images and only the classification stage needs to be optimized. In such embodiments, the feature vectors for the each image in the dataset are pre-calculated with the feature extraction stage. These feature vectors can then be formed into a feature matrix by stacking the feature vectors such that the feature matrix has a width equal to the size of the feature vectors and a height equal to the number of images in the dataset and processed by the feature extraction stage. The feature matrix is stored in a storage location. Such storage may improve a speed of training of the classification stage. In some instances, the time to train the classification stage can be improved by an order of 100 or 1000 times as compared to calculating the image feature vectors for each training image of the dataset when training the classification stage.

Such efficiency improvements are especially advantageous during hyperparameter optimization of the classification stage, where an architecture of the machine learning model including the feature extraction stage and classification stage is repeatedly adjusted and the classification stage is trained based on the stored feature matrix. Hyperparameter optimization may correspond to selection of aspects of the architecture of the classification stage to improve the classification capabilities of the classification stage. Such selection (and, thus, the hyperparameter optimization) may be made by the operator or a user of the machine learning model or a system using the machine learning model.

In some instances, optimizing the hyperparameter(s) comprises applying an algorithm to select candidate values for the hyperparameters from available distributions or a list of available values for each hyperparameter. Other methods of selecting the candidate values are understood to be available for use in selecting the candidate values. The machine learning model with the architecture generated based on the selected hyperparameters may then be trained and evaluated using at least a portion of the dataset of labeled images (for example, a 5-fold cross validation of the training set of the dataset). If the value selected for any of the hyperparameters is at an edge of the available range for that hyperparameter, the range for that hyperparameter may be extended, and the hyperparameter optimization should be repeated until no hyperparameter is at the edge of its corresponding range and performance of the classification model meets desired thresholds and parameters, for example values as identified from testing the machine learning model with a set of training images. A selected listing of preferred hyperparameters, and corresponding ranges of values, include:

A learning rate for the classification stage fitting algorithm
Values: [0.001, 0.0003, 0.0001, 0.00003, 0.00001, 0.000003]
A number of epochs to train the classification stage
Values: Uniform(500, 10000)
A learning optimizer
Values: [Adam, SDG, RMSprop, Adadelta, Adagrad, Adamax, Nadam]
A batch size
Values: [8, 16, 32, 64, 128]
A number of hidden layers
Values: [1, 2, 3, 4, 5, 6, 7, 8, 9]
A size of each hidden layer
Values: Uniform(128, 2048)

Regularization weights and strategies (for example, L1, L2, drop out, and/or the like)
L1 Values: [0.0, 0.01, 0.003, 0.001, 0.0003, 0.0001, 0.00003, 0.000001, 0.0000003]
L2 Values: [0.0, 0.01, 0.003, 0.001, 0.0003, 0.0001, 0.00003, 0.000001, 0.0000003]
Drop out % Values: [0, 0.001, 0.003, 0.01, 0.03, 0.1, 0.3, 1.0, 3.0, 10.0, 20.0, 30.0, 40.0, 50.0]
A loss function
Value: [binary_crossentropy]
An activation function for the layers
Value: [RELU]

In some instances, further optimization of the machine learning model can include retraining the feature extraction stage. Such optimization may include retraining the weights of the feature extraction stage and/or also include hyperparameter optimization of the architecture of the feature extraction stage. In some instances, an additional output layer can be added to the classification stage. The additional output layer may provide for applying regression to score image quality.

In some embodiments, training the machine learning model comprises implementing the machine learning model with pre-trained weights for the VGG16 CNN feature extraction stage. Thus, the VGG16 CNN weights may be fully specified, leaving only the weights for the classification stage to be determined via training. The training may comprise processing labeled images having three channels and a size of 480×480 pixels from the data set or repository with the VGG16 CNN stage. The VGG16 CNN stage may output the feature vector (for example, the feature vector 206) having a length of 512 elements or samples. The feature vector may represent a collection of image features suitable for classification tasks as performed by the classification stage. The collection of image features of the feature vector may include features for a large range of image types (for example, the interferogram type images, wide view type images, and focus view type images). Processing the feature vector from the VGG16 CNN stage by the fully connected classification stage produces an output vector that represents the probabilities of the presence of each of the artifacts in the image processed by the machine learning model.

Example Images Classified by the Aspects Herein

FIGS. 4A-4G depict example images that may exist in the image dataset and/or are captured by the camera of the system 100 of FIG. 1.

Figure 4B:
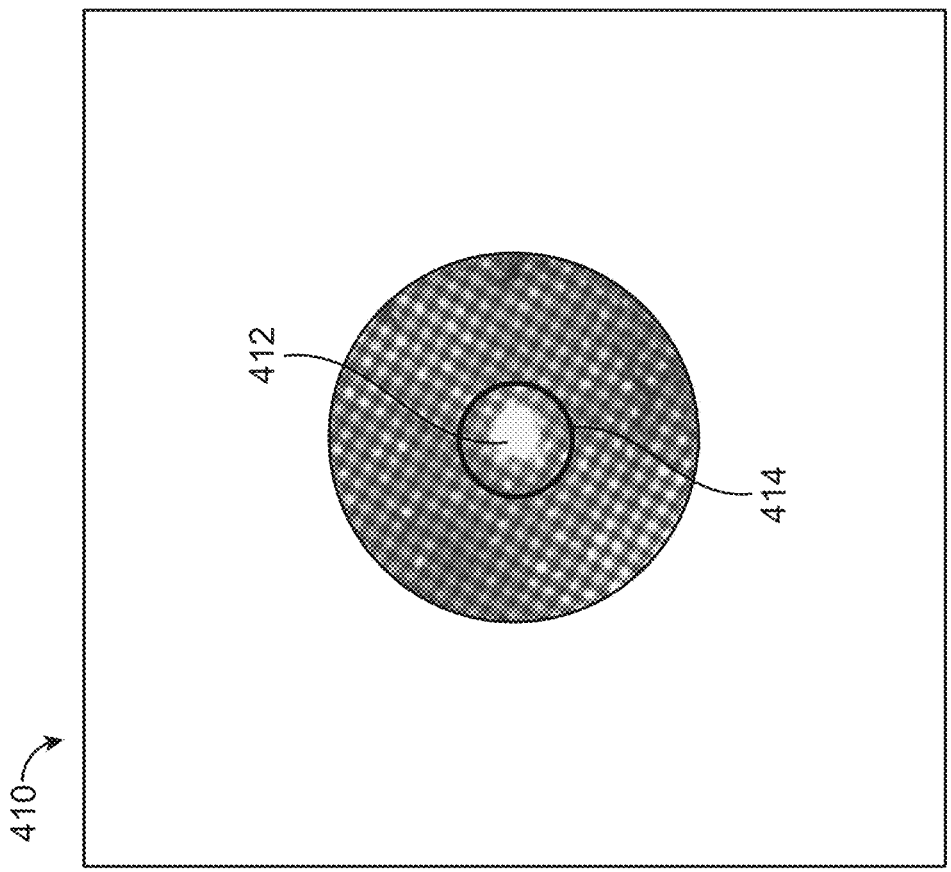
FIGS. 4A-4G depict images that may exist in an image dataset and/or are captured by one or more cameras of the system of FIG. 1, in accordance with certain embodiments.
Figure 4A:
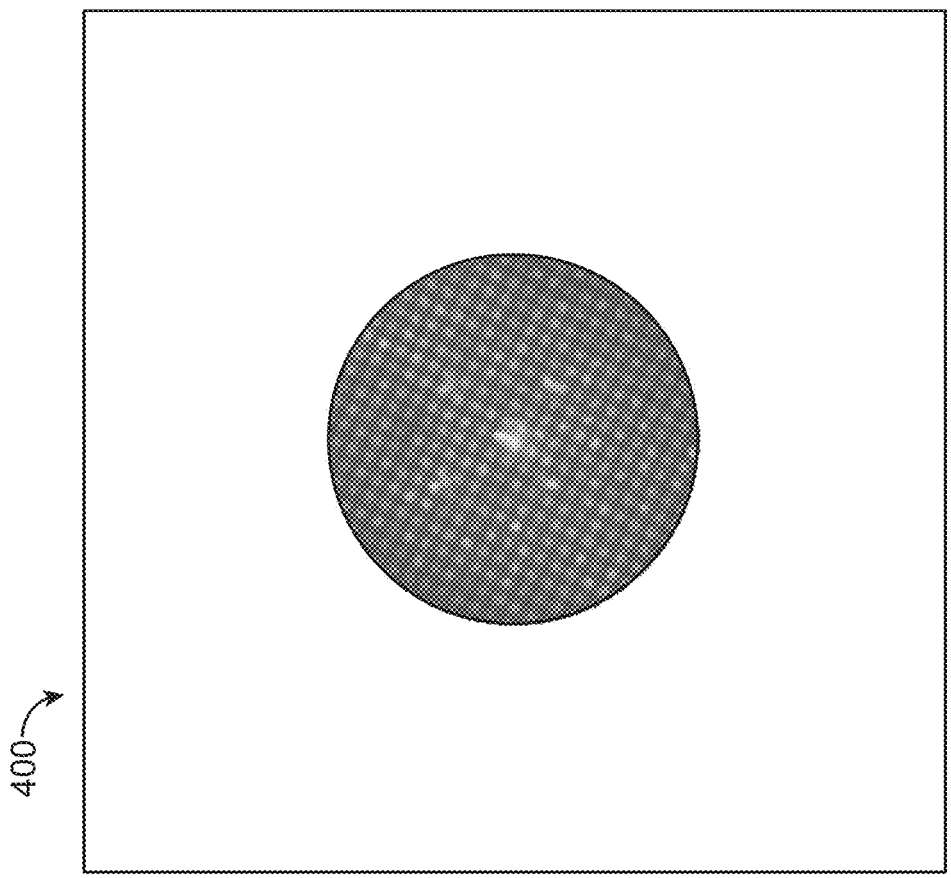

FIG. 4A depicts an image 400 that is an example of a Talbot-Moire image of a patient's eye 110 that does not include any artifacts. As shown, the image 400 does not include any exceedingly bright areas of light or reflection or any objects or regions of haziness or abstraction in the patient's eye 110.

FIG. 4B depicts an image 410 that is an example of a Talbot-Moire image of a patient's eye 110 that includes a glint artifact 412. Specifically, the glint artifact 412, which is caused by excessive reflection of a light source off a portion of the patient's eye 112, is shown approximately at a center of the image 410.

In the example use cases introduced above, the user interface 108 may present the operator with the image 410. More specifically, when the image 410 includes the glint artifact 412, the user interface 108 optionally or selectively displays the image 410 with an identifier 414 to specifically identify a location of the glint artifact 412. In some instances, the identifier 414 may represent any shape or object used to draw attention of a viewer or system to a particular location or locations of the image 410. In some instances, the user interface 108 will also include a message to the operator that the image is believed to include the glint artifact 412 at the location(s) identified by the identifier 414. In some instances, the user interface 108 will only show the identifier 414 when the probability that the image 410 includes the glint artifact 412 exceeds a specified threshold (i.e., that the quality value for the image 410 drops below the specified threshold).

Figure 4D:
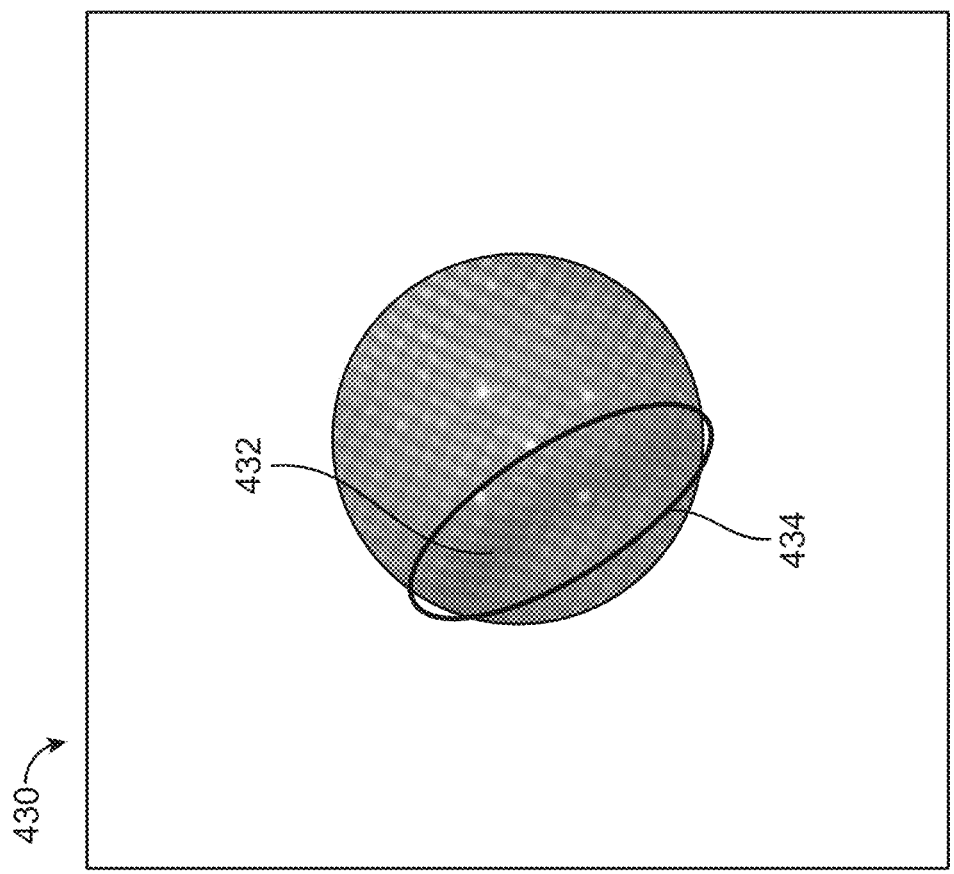
Figure 4C:
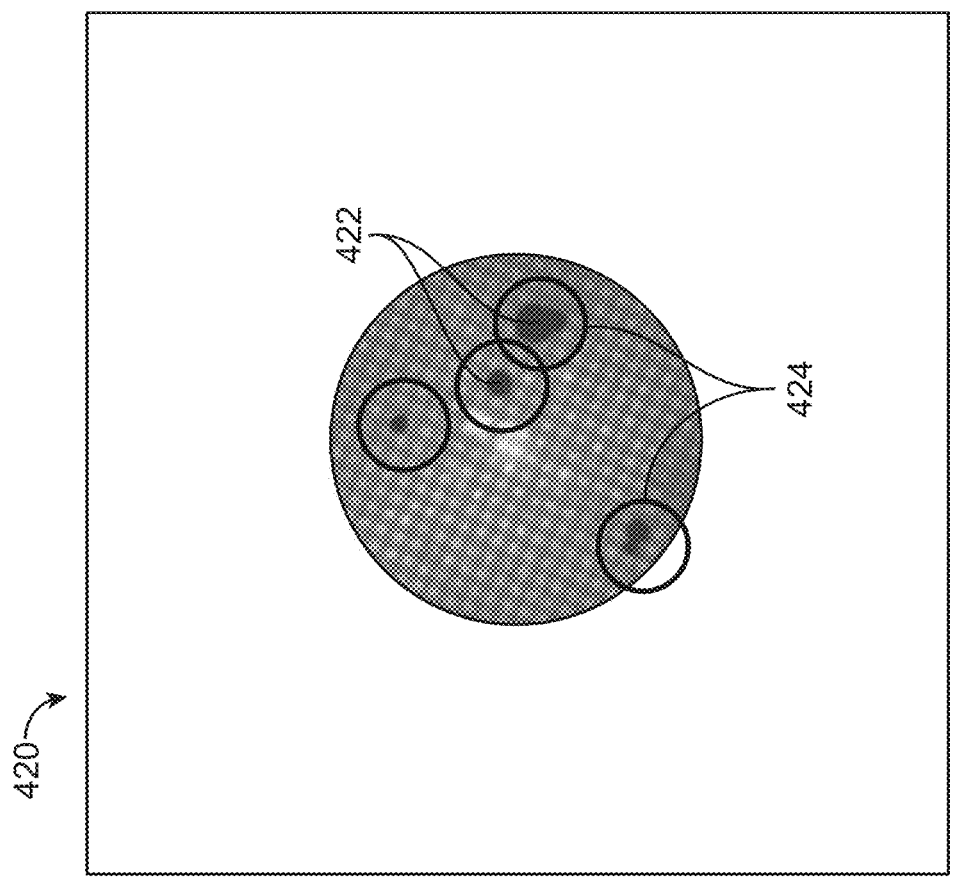

FIG. 4C depicts an image 420 that is an example of a Talbot-Moire image of a patient's eye 110 that includes a number of bubble artifacts 422. Specifically, the bubble artifacts 422 are shown in multiple locations around the patient's eye in the image 420.

In the example use cases introduced above, the user interface 108 may present the operator with the image 420. More specifically, when the image 420 includes the bubble artifacts 422, the user interface 108 optionally or selectively displays the image 420 with identifiers 424 to specifically identify the one or more locations of the bubble artifacts 422. In some instances, the identifiers 424 may represent any shape or object used to draw attention of a viewer or system to a particular location or locations of the image 420. In some instances, the user interface 108 will also include a message to the operator that the image is believed to include the bubble artifact 422 at the location(s) identified by the identifier 424. In some instances, the user interface 108 will only show the identifier 424 when the probability that the image 420 includes the bubble artifacts 422 exceeds a specified threshold (i.e., that the quality value for the image 420 drops below the specified threshold).

FIG. 4D depicts an image 430 that is an example of a Talbot-Moire image of a patient's eye 110 that includes a floater artifact 432. Specifically, the floater artifact 432 is shown across a region in the patient's eye in the image 430.

In the example use cases introduced above, the user interface 108 may present the operator with the image 430. More specifically, when the image 430 includes the floater artifact 432, the user interface 108 optionally or selectively displays the image 430 with an identifier 434 to specifically identify a location of the floater artifact 432. In some instances, the identifier 434 may represent any shape or object used to draw attention of a viewer or system to a particular location or locations of the image 430. In some instances, the user interface 108 will also include a message to the operator that the image is believed to include the floater artifact 432 at the location(s) identified by the identifier 434. In some instances, the user interface 108 will only show the identifier 434 and message when the probability that the image 430 includes the floater artifact 432 exceeds a specified threshold (i.e., that the quality value for the image 430 drops below the specified threshold).

Figure 4F:
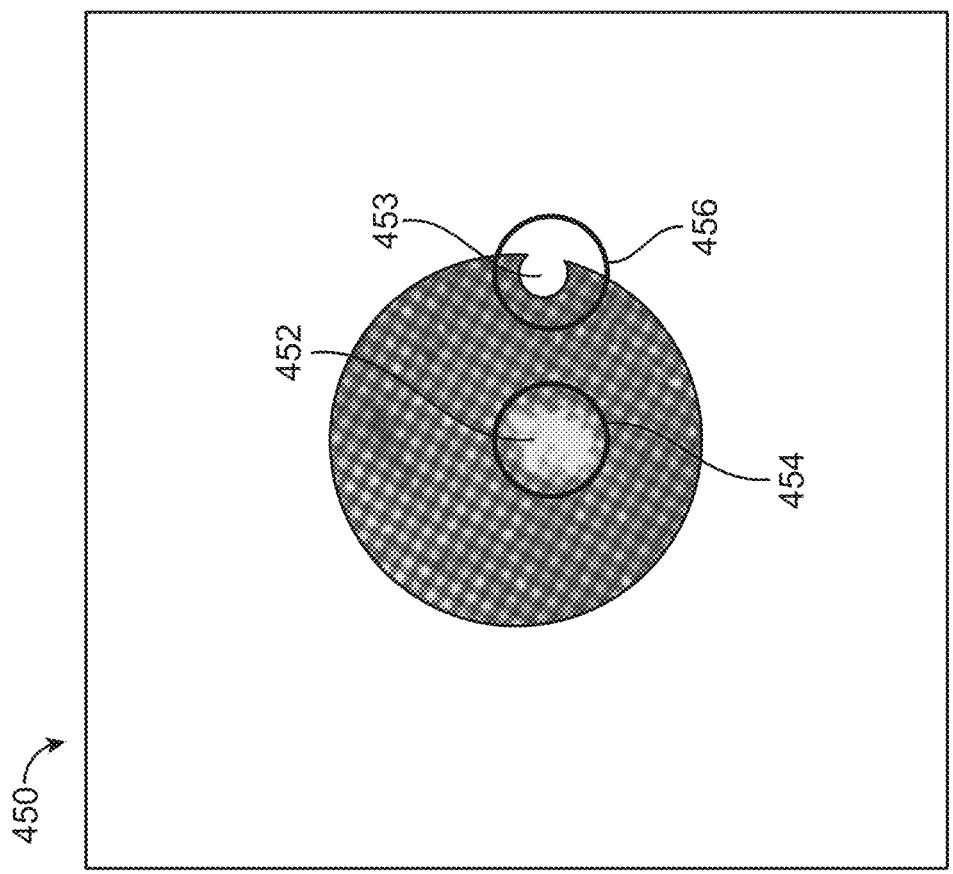
Figure 4E:
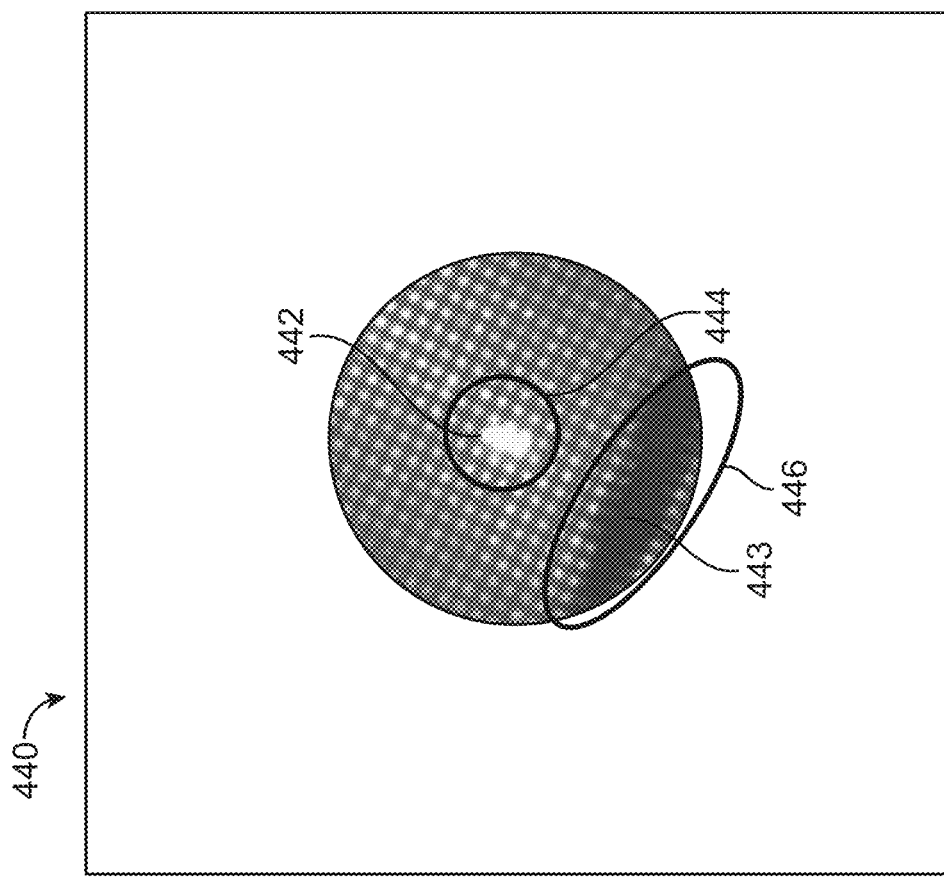

FIG. 4E depicts an image 440 that is an example of a Talbot-Moire image of a patient's eye 110 that includes both a glint artifact 442 and a floater artifact 443. Specifically, the glint artifact 442 is shown near a center of the patient's eye and the floater artifact 443 is shown across a region in the patient's eye in the image 440.

In the example use cases introduced above, the user interface 108 may present the operator with the image 440. More specifically, when the image 440 includes the glint artifact 442 and the floater artifact 443, the user interface 108 optionally or selectively displays the image 440 with an identifier 444 to specifically identify a location of the glint artifact 442 and an identifier 446 to identify a location or region of the floater artifact 443.

In some instances, the identifiers 444 and 446 may represent any shapes or objects used to draw attention of a viewer or system to a particular location or locations of the image 440. In some instances, the user interface 108 will also include a message to the operator that the image is believed to include the glint artifact 442 and the floater artifact 443 at the respective location(s) identified by the identifier 444 and identifier 446. In some instances, the user interface 108 will only show the identifiers 444 and 446 when the probabilities that the image 440 includes the glint artifact 442 and the floater artifact 443 exceed corresponding specified thresholds (i.e., that the quality value for the image 440 drops below the specified thresholds).

FIG. 4F depicts an image 450 that is an example of a Talbot-Moire image of a patient's eye 110 that includes both a glint artifact 452 and a bubble artifact 453. Specifically, the glint artifact 452 is shown near a center of the patient's eye and the bubble artifact 453 is shown along a right edge of the patient's eye in the image 450.

In the example use cases introduced above, the user interface 108 may present the operator with the image 450. More specifically, when the image 450 includes the glint artifact 452 and the bubble artifact 453, the user interface 108 optionally or selectively displays the image 450 with an identifier 454 to specifically identify a location of the glint artifact 452 and an identifier 456 to identify a location or region of the bubble artifact 453. In some instances, the identifiers 454 and 456 may represent any shapes or objects used to draw attention of a viewer or system to a particular location or locations of the image 450. In some instances, the user interface 108 will also include a message to the operator that the image is believed to include the glint artifact 452 and the bubble artifact 453 at the respective location(s) identified by the identifier 454 and identifier 456. In some instances, the user interface 108 will only show the identifiers 454 and 456 when the probabilities that the image 450 includes the glint artifact 452 and the bubble artifact 453 exceed corresponding specified thresholds (i.e., that the quality value for the image 450 drops below the specified thresholds).

Figure 4G:
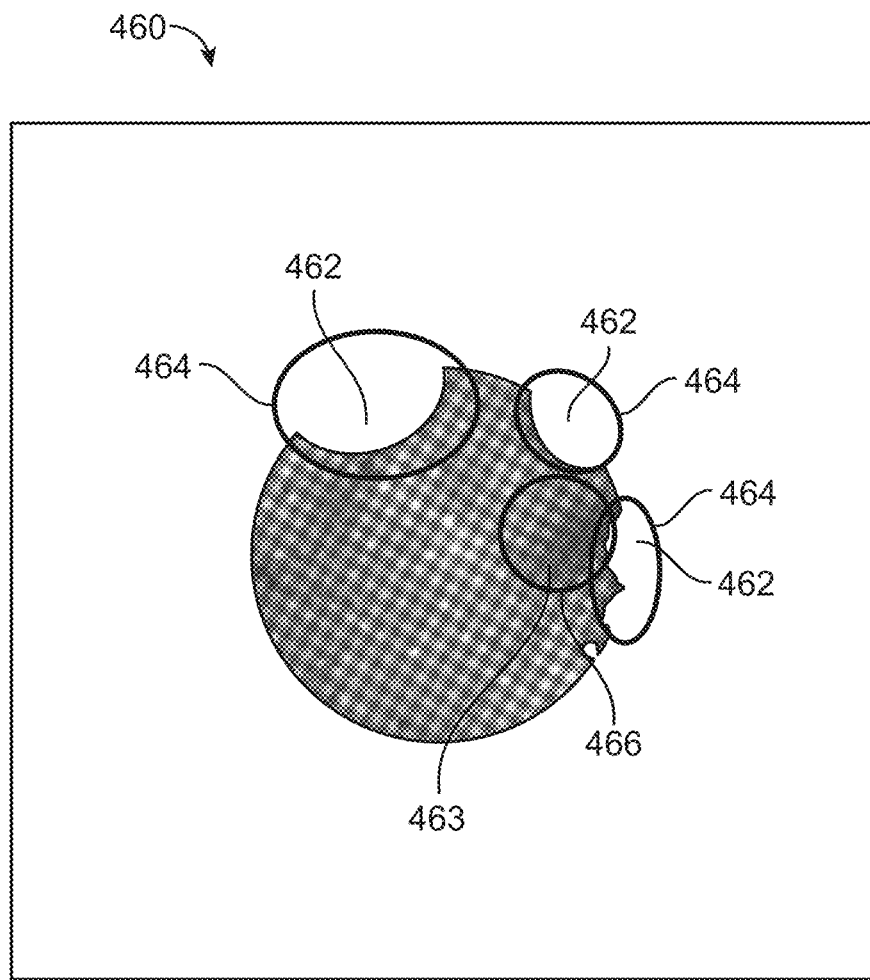

FIG. 4G depicts an image 460 that is an example of a Talbot-Moire image of a patient's eye 110 that includes both multiple bubble artifacts 462 and a floater artifact 463. Specifically, the bubble artifacts 462 are shown along top and right edges of the patient's eye and the floater artifact 463 is shown across a region in the patient's eye in the image 460.

In the example use cases introduced above, the user interface 108 may present the operator with the image 460. More specifically, when the image 460 includes the bubbles artifacts 462 and the floater artifact 463, the user interface 108 optionally or selectively displays the image 460 with identifiers 464 to specifically identify locations of the bubbles artifacts 462 and an identifier 466 to identify a location or region of the floater artifact 463. In some instances, the identifiers 464 and 466 may represent any shapes or objects used to draw attention of a viewer or system to a particular location or locations of the image 460. In some instances, the user interface 108 will also include a message to the operator that the image is believed to include the bubbles artifact 462 and the floater artifact 463 at the respective location(s) identified by the identifier 464 and identifier 466. In some instances, the user interface 108 will only show the identifiers 464 and 466 when the probabilities that the image 460 includes the bubbles artifact 462 and the floater artifact 463 exceed corresponding specified thresholds (i.e., that the quality value for the image 460 drops below the specified thresholds).

As introduced above, images of the patient's eye that do not include any artifacts may be processed to generate measurements or corresponding information for use during the procedure. In some instances, the system may determine that one or more images that do include artifacts can still be processed into measurements for use during the procedure. For example, if the artifact included in the image is of a sufficiently small size or located in a particular region where its existence has minimal impact on the measurements, the operator and/or the system may determine that the image can proceed to processing for measurements based thereon.

In some instances, various factors may be used to determine whether or not the image 112 including the one or more artifacts can progress to measurement determination. The operator or the system 100 may determine that the image 112 including one or more artifacts proceeds to measurement generation based on one or more of a size of the artifact in the image 112, a location of the artifact in the image 112, and a type of artifact in the image 112. Specifically, when the determination is made based on a probability that the image 112 includes an artifact, as introduced above with respect to the quality bar graph and/or quality values, the determination may further be made based on an analysis of whether the location, size, and/or type of artifact would detrimentally impact measurements generated based on the image 112. For example, if the image 112 includes a single bubble artifact along an edge of the patient's eye 110 and having a size that covers less than a threshold of the patient's eye 110, then the system 100, or the operator, may determine that the image 112 including the bubble artifact can still be used for measurement data generation. Alternatively, if the image 112 includes multiple bubble artifacts near a center of the patient's eye 110 and having a combined size that covers more than a threshold of the patient's eye 110, then the system 100, or the operator, may determine that the image 112 including the bubble artifact cannot be used for measurement data generation.

Such determinations to use images including one or more artifacts to generate measurement data may be image specific based on a variety of factors. The variety of factors may include a number of artifact free images available of the patient's eye, a type of artifact in images including at least one artifact, a size of the artifact in the images including the at least one artifact, a location of the artifact in the images including the at least one artifact, and the like.

Figure 5:
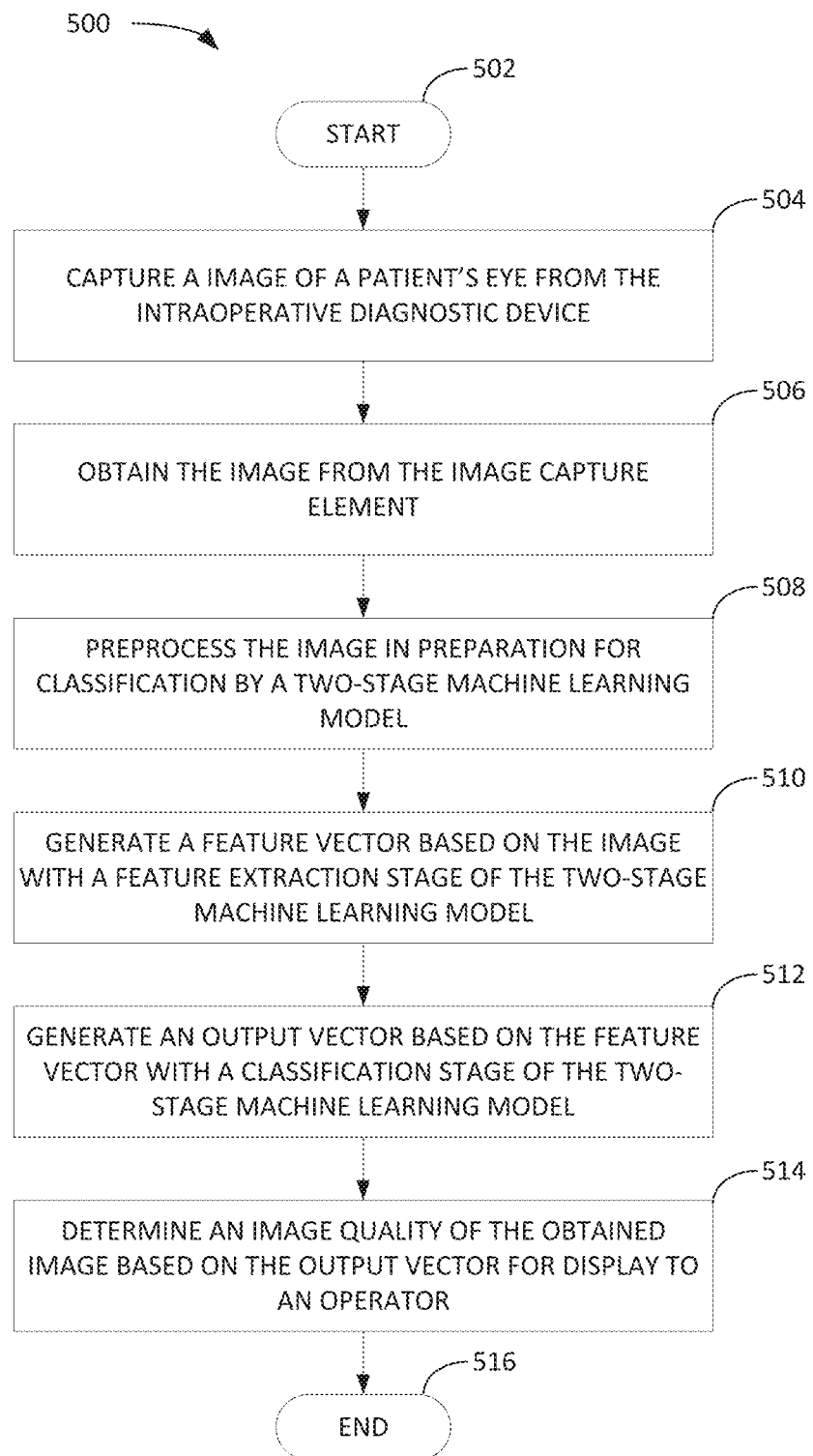
FIG. 5 depicts a method for identifying digital images that include one or more artifacts detrimental to image processing and analysis using a machine learning model, in accordance with certain embodiments.

Example Method of Real-Time Processing of Image Data to Identify Artifacts Therein FIG. 5 depicts an example method 500 identifying digital images that include one or more artifacts. For example, the controller 106 and/or the system 100 of FIG. 1 may be configured to perform the method 500, for example, based on the machine learning models of FIGS. 2A and 2B.

Method 500 starts at block 502 and, at block 504, begins with capturing an image (for example, the image 112 of a patient's eye 110) based on operations of an imaging device (for example, the aberrometer 104). In some instances, one or more of the cameras of the system 100 may capture the image. In some instances, the image may comprise a color image (for example, including three channels of data, one for each of the red, green, and blue layers) or a grayscale image. Furthermore, the image may have a first size, as measured in pixels (for example, 640×480 pixels).

The method 500 continues, at block 506, with obtaining the image from an image capture element. The method 500 may obtain the image from the camera, as described above, where the camera corresponds to the image capture element.

In some embodiments, obtaining the image comprises receiving the image 112 from the camera or aberrometer 104, as shown in FIG. 1.

The method 500 then proceeds to block 508 with preprocessing the image in preparation for classification by a machine learning model. In some embodiments, the machine learning model is a two-stage machine learning model, as described above with reference to FIGS. 2A-3C. In some embodiments, the preprocessing of block 508 is optional. For example, as explained herein, preprocessing may only be required when the image needs to be processed to present it as suitable input to a machine learning model. The preprocessing can involve adjusting one or more of the size of the image, the format of the pixels in the image, the number of channels in the image, and/or selection of a region of interest for the image.

In some instances, preprocessing the image comprises preprocessing the image 112 with the preprocessing module 201 to generate the input image 202 for input to the machine learning model 203, as shown in FIGS. 2A-2B.

The method 500 then proceeds to block 510 with generating a feature vector based on the preprocessed image with a feature extraction stage of the two-stage machine learning model. In some embodiments, the feature extraction stage is the first stage of the machine learning model and comprises the VGG16 CNN introduced above. Alternatively, the feature extraction stage may comprise corresponding features or stages of any other neural network, for example VGG19, ResNet50, Inception V3, Xception, and the like. The feature vector generated by the method 500 may comprise an output vector.

In some instances, block 510 corresponds to processing the preprocessed input image 202 with the first stage 204 of the machine learning model 203 to generate the feature vector 206, as shown in FIGS. 2A-2B.

The method 500 then proceeds to block 512 with generating an output vector (for example, one of the artifact probabilities 210, 212, or 214) based on the feature vector with a classification stage of the two-stage machine learning model. In some instances, the output vector generated at block 512 comprises a combination of output vectors for all artifact types that the machine learning model is configured to identify. This classification stage may comprise one or more fully-connected layers and an output layer having neurons that apply an activation function to generate the output vector. In some embodiments, the activation function of the output layer neurons may comprise the sigmoid or logistic activation function. In other examples, the activation function could comprise other functions, such as a softmax activation function, or another activation function that can provide probability outputs.

In some instances, block 512 corresponds to processing the feature vector 206 with the second stage 208 of the machine learning model 203 to generate the artifact probabilities 210, 212, and 214, as shown in FIGS. 2A-2B. For example, the generated output vector may comprise each of the artifact probabilities 210, 212, and 214 or may comprise any combination of one or more of the artifact probabilities 210, 212, or 214. In some embodiments, the classification stage corresponds to the second stage 208 of the machine learning model 203.

The method 500 then proceeds to block 514 with determining an image quality of the obtained image 112 based on the output vector for display to an operator. In some embodiments, the output vectors provide probability information regarding a probability that the image includes one or more artifacts. In some instances, the quality of the image can be determined based on this probability according to Eq. 1, above. Thus, the image quality may be indicative of the probability that the image includes an artifact, where inclusion of the artifact may interfere with a measurement of refraction and other data of the patient's eye. The method 500 then ends at block 516.

For example, the output vector representing the artifact probabilities 210, 212, and 214 may indicate that the image 112 has a probability of 0.75 with regard to including a bubble artifact, .01 with regard to including a glint artifact, and 0.24 with regard to including a floater artifact.

As introduced above, the method 500 may generally be performed repeatedly or iteratively for each image generated by the aberrometer 104 or camera(s) of the system 100.

Notably, FIG. 5 is just one example method, and other methods having additional, different, and/or fewer steps (or blocks) are possible consistent with the various embodiments described herein.

Figure 6:
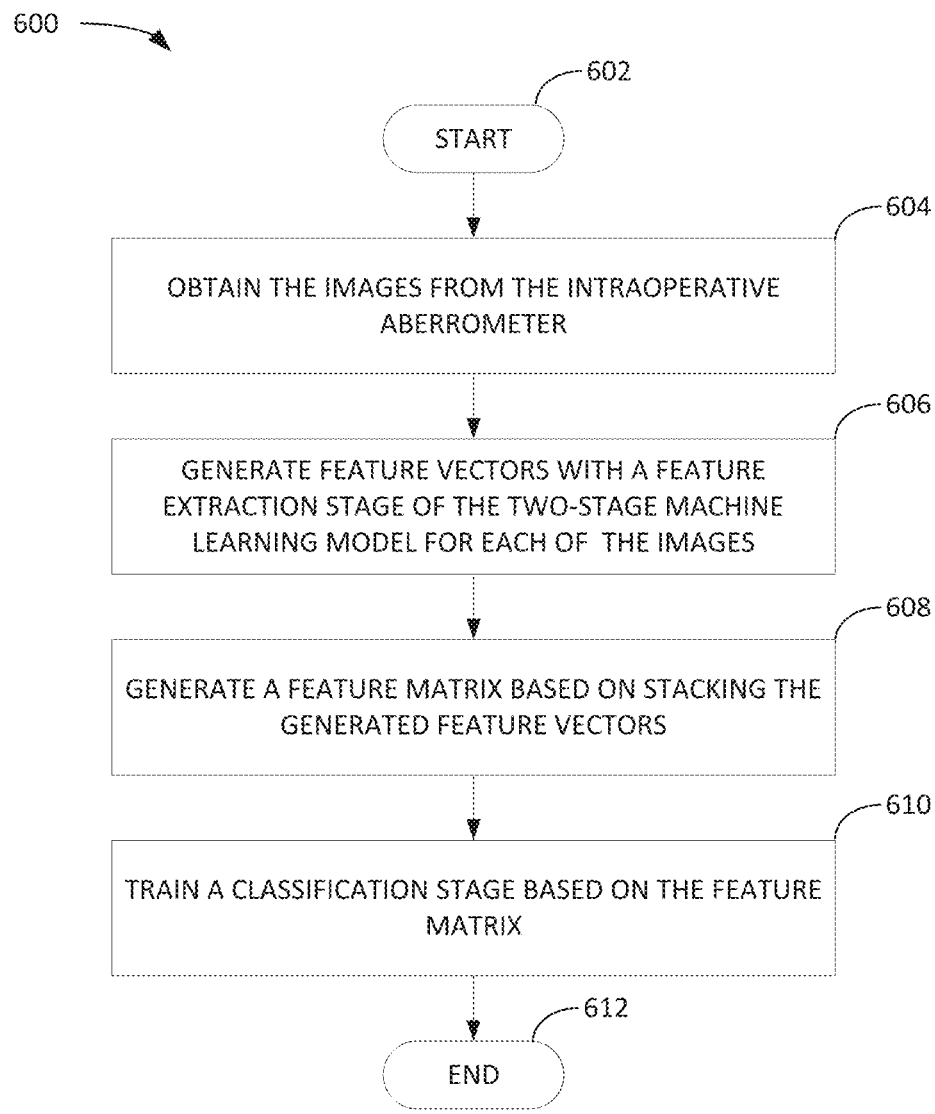
FIG. 6 depicts a method for training a machine learning model to identify digital images that include one or more artifacts detrimental to image processing and analysis, in accordance with certain embodiments.

Example Method of Training a Machine Learning Model for Processing Image Data to Identify Artifacts Therein FIG. 6 depicts an example method 600 for training a machine learning model to identify digital images that include one or more artifacts. The training of the machine learning model may be completed by one or more of the controller 106 and/or the system 100 of FIG. 1 or a component or system external to the system 100. The method 600 may be used to train, for example, the machine learning models of FIGS. 2A and 2B. In some embodiments, the method 600 only trains the second stage 208, 218, and/or 228 (i.e., the classification stage) and the first stage 204 (i.e., the feature extraction stage) is not trained.

Method 600 starts at block 602 and, at block 604, begins with obtaining the images that will be used to train the machine learning model. In some instances, the images are obtained in real-time from an image capture devices (for example, the aberrometer 104 and/or one or more of the cameras of the system 100). In some instances, the images are obtained from a data store, for example, a database of images for use in training machine learning models. In some instances, the obtained images are labeled with respect to whether or not they include artifacts and, if so, what artifacts they include.

The method 600 continues, at block 606, with generating feature vectors with a feature extraction stage of the two-stage machine learning model for each of the images. As introduced above, the feature extraction stage generates the feature vectors based on applying the feature extraction stage (for example, the first stage 204 of the machine learning model 203) to the images, for example the feature extraction stage having the VGG16 CNN architecture. In some instances, other feature extraction stages can be implemented for the feature extraction stage of the machine learning model (for example, VGG19, and so on). In some embodiments, the feature vectors for each of the images have the same dimensions (for example, dimensions of 1×512 elements or samples).

The method 600 continues, at block 608, with generating a feature matrix based on stacking the generated feature vectors. Stacking the generated feature vectors may comprise merely creating a matrix out of a number of the feature vectors by placing them one on top of another to create the feature matrix. The feature matrix will have dimensions of the length of the feature vector and a height of the number of feature vectors stacked together. For the example use case herein, the feature matrix may be generated by stacking the feature vectors 206 generated by the first stage 204 for each image processed by the first stage 204 and the machine learning model 203 (for example, all images of the dataset).

The method 600 continues at block 610 with training a classification stage based on the feature matrix. In some instances, the classification stage (i.e., the second stage 208) comprises employing the feature matrix generated based on the obtained training images to train the classification stage to properly identify artifacts in images processed by the classification stage. Properly identifying the artifacts may comprise the second stage 208 generating outputs that identify high probabilities of artifacts when the images do contain artifacts and low probabilities of artifacts when the images do not include artifacts. In some embodiments, the activation function(s) for the second stage 208 may be varied as part of the training of the classification stage. In some embodiments, the trained second stage 208 may then be used to determine whether images received in real-time from a diagnostic imaging device used during one or more procedures (for example, the aberrometer 104) include one or more artifacts. The method 600 then ends at block 612.

As introduced above, the method 600 may generally be performed repeatedly or iteratively.

Notably, FIG. 6 is just one example method, and other methods having additional, different, and/or fewer steps (or blocks) are possible consistent with the various embodiments described herein.

Example Processing Systems

Figure 7:
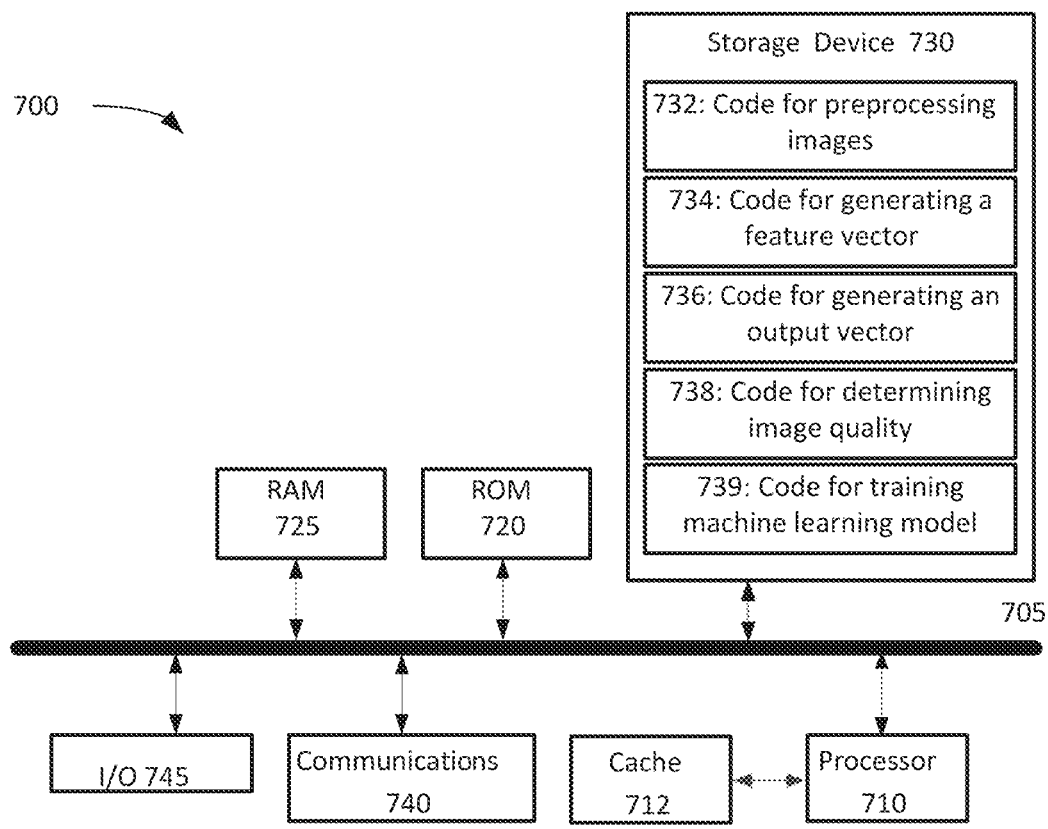
FIG. 7 is a diagram of an embodiment of a processing system that performs or embodies aspects described herein, in accordance with certain embodiments.

FIG. 7 is a diagram of an embodiment of a processing system or device. According to some embodiments, the processing system of FIG. 7 is representative of a computing system that may be included in one or more of intraoperative aberrometry systems that implement the machine learning model processing described herein, with reference to the aberrometer 104, the controller 106, the user interface 108, and/or the like. Specifically, the processing system of FIG. 7 may implement one or more of the machine learning models 203, 217, and 227 according to the data flows 200, 250a, 250b, and 250c and otherwise introduced and discussed herein to identify artifacts in image data of patient eye images, as shown in FIGS. 4A-4G, and/or the like.

FIG. 7 illustrates a computing system 700 where the components of system 700 are in electrical communication with each other. The system 700 includes a processor 710 and a system bus 705 that couples the various components. For example, the bus 705 couples the processor 710 to various memory components, such as a read only memory (ROM) 720, a random access memory (RAM) 725, and/or the like (e.g., PROM, EPROM, FLASH-EPROM, and/or any other memory chip or cartridge). The system 700 may further include a cache 712 of high-speed memory connected to (directly or indirectly), in close proximity to, or integrated as part of the processor 710. The system 700 may access data stored in the ROM 720, the RAM 725, and/or one or more storage devices 730 through the cache 712 for high-speed access by the processor 710. In some examples, the cache 712 may provide a performance boost that avoids delays by the processor 710 in accessing data from the ROM 720, the RAM 725, and/or the one or more storage devices 730 previously stored in cache 712. In some examples, the one or more storage devices 730 store one or more software modules (e.g., software modules 732, 734, 736, 738, 739, and/or the like). The software modules 732, 734, 736, 738, and/or 739 may control and/or be configured to control the processor 710 to perform various actions, such as the processes of methods 500 and/or 600. In some aspects, one or more of the software modules 732, 734, 736, 738, and/or 739 include details for the machine learning models 203, 217, and/or 227 described herein. Some instances may include additional or fewer software modules and/or code to program the processor 710 to perform other functions.

In some embodiments, the software module 732 comprises instructions that program the processor 710 to pre-process images. The code for preprocessing the images may cause the processor 710 (or any other component for the computing system 700 or any other computing system) to preprocess images 112 generated by the aberrometer 104 and/or the cameras of the system 100. The processor 710 may one or more of adjust a size of the image 112, a format of the pixels of the image 112, identify a region of interest in the image 112, or change a number of channels for the image 112, thereby generating the input image 202.

In some embodiments, the software module 734 comprises instructions that program the processor 710 to generate a feature vector. The code for generating the feature vector may cause the processor 710 (or any other component for the computing system 700 or any other computing system) to apply the first stage 204 of the machine learning model 203 (or corresponding machine learning model 203) to process and analyze the input image 202 to generate the feature vector. The first stage 204 of the machine learning model 203 may comprise any feature generating neural network component, such as the VGG16 CNN, and/or the like.

In some embodiments, the software module 736 comprises instructions that program the processor 710 to generate an output vector. The code for generating the output vector may cause the processor 710 (or any other component for the computing system 700 or any other computing system) to apply the second stage 208 of the machine learning model 203 (or corresponding machine learning model 203) to process and analyze the feature vector to generate the output vector. The second stage 208 of the machine learning model 203 may comprise any classification neural network component, such as the fully-connected layers with an output layer using the sigmoid activation function to generate the output vector that identifies the probability that the processed image includes a corresponding artifact.

In some embodiments, the software module 738 comprises instructions that program the processor 710 to determine an image quality based on the generated output vector. The code for determining the image quality may cause the processor 710 (or any other component for the computing system 700 or any other computing system) to analyze the probability identified in the output vector to determine a corresponding image quality based on the probability in the output vector.

In some embodiments, the software module 739 comprises instructions that program the processor 710 to train the machine learning model 203. The code for training the machine learning model may cause the processor 710 (or any other component for the computing system 700 or any other computing system) to train one or more of the first stage 204 or the second stage 208 of the machine learning model 203 (or corresponding machine learning model 203). In some instances, training the stages may comprise using a data set of labeled images to identify and train parameters, weights, and/or biases of the corresponding stages based on the labeled images to enable the stages to classify images according to the labels.

Although the system 700 is shown with only one processor 710, it is understood that the processor 710 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, the system 700 may be implemented as a stand-alone subsystem and/or as a board added to a computing device or as a virtual machine, or as a cloud-based processing machine.

To enable user interaction with the system 700, the system 700 includes one or more communication interfaces 740 and/or one or more input/output (I/O) devices 745. In some examples, the one or more communication interfaces 740 may include one or more network interfaces, network interface cards, and/or the like to provide communication according to one or more network and/or communication bus standards. In some examples, the one or more communication interfaces 740 may include interfaces for communicating with the system 700 via a network. In some examples, the one or more I/O devices 745 may include on or more user interface devices (e.g., keyboards, pointing/selection devices (e.g., mice, touch pads, scroll wheels, track balls, touch screens, and/or the like), audio devices (e.g., microphones and/or speakers), sensors, actuators, display devices, and/or the like).

Each of the one or more storage devices 730 may include non-transitory and non-volatile storage such as that provided by a hard disk, an optical medium, a solid-state drive, and/or the like. In some examples, each of the one or more storage devices 730 may be co-located with the system 700 (for example, a local storage device) and/or remote from the system 700 (for example, a cloud storage device).

According to some embodiments, the system 700 may provide a graphical user interface (GUI) suitable for aiding a user (e.g., a surgeon and/or other medical personnel or operator) in the performance of the processes of methods 500 and/or 600. For example, the GUI may provide the user interface 108 of FIG. 1. The GUI may include depictions of images captured by the system 100, the quality bar graphs and other information generated by the machine learning models 203, 217, and/or 227, instructions or recommendations to the operator regarding whether to keep or exclude the image with respect to processing, identification of artifacts within images of a patient's eye (for example, as depicted in FIGS. 4A-4G), requests for operator input, messages to the operator, and/or the like. In some examples, the GUI may display true-color and/or grayscale images of the patient's eye, and/or the like.

Example Displays of Classified Images

FIGS. 8A-8O are display concepts for providing digital images of the patient's eye to a user with details of an image quality and/or any detected artifacts via a graphical user interface, according to a plurality of embodiments. These display concepts depict different ways to present an operator with information regarding images of the patient's eye, namely whether the images include any artifacts and the quality of the image. Furthermore, the display concepts may identify locations for any included artifacts, as well as metrics of the images, such as whether the image is a "good"

or "bad" image and/or a quality of the image, and so forth. Note that FIGS. 8A-8O are just some examples, and other implementations are possible.

FIG. 8A shows a display concept 800 of a basic display of a "good" image 820 and a label 822 identifying an image quality of the image 820, here including the text "Good Image." In certain embodiments, "good" image comprises an image of the patient's eye that does not include any artifacts or that can otherwise be processed for one or more measurements of the patient's eye. The classification of "good image" is for the image 820 as a whole and indicates that there are no significant artifacts present. The label 822 may comprise any textual label that uses one or more words to describe an image quality of the image 820, evaluated based on whether the imaging system is able to process the corresponding image for the one or more measurements of the patient's eye. Thus, when the image 820 is a good image, then the label 822 may identify the image as such a "Good Image". In some embodiments, the image of the patient's eye including one or more artifacts may be labeled as a "Good Image" when the one or more artifacts do not impair an ability to process the image for measurements of the patient's eye, such as when the artifacts are less than a threshold size or in a particular region of the patient's eye, and the like.

FIG. 8B shows a display concept 801 of another display of the "good" image 820, the label 822 identifying the image quality of the image 820, and a visual or gradient legend or scale (referred to herein as "visual legend") 824 showing a relative image quality of the image 820. The visual legend 824 may comprise a range of colors, hues, grayscales, patterns, and/or the like that uses a scheme or scale of image values going from a first value (for example, at the bottom), to a second value (for example, at the top). In some embodiments, the orientation of the visual legend 824 can be adjusted to be horizontal, diagonal, and so forth. In some embodiments, the first value of the visual legend 824 indicates a poor or bad quality image. The visual legend 824 may indicate a progression of the image quality of the image 820 from the first value (poor quality image) increasing in image quality to the second value, which indicates a high or good quality image. The visual legend 824 may include an arrow 826 that indicates where the image quality for the image 820 falls on the visual legend 824 with respect to the image quality of the image 820. In FIG. 8B, the arrow 826 indicates that the image 820 is a good image when the arrow 826 identifies the image quality as being near the second value in the visual legend 824. The label 822 includes the text "good image," where the good image is classified as described above.

FIG. 8C shows a display concept 802 of another display of the "good" image 820, the label 822 identifying the image quality of the image 820, and a visual signal 828 showing a relative image quality of the image 820. The visual signal 828 may comprise different colors, hues, grayscales, patterns, and/or the like to indicate different information about the image 820, for example, like a traffic light. Similar to the visual legend 824, the visual signal 828 may include different indicators for different image qualities, including bad or poor image quality (on the left), marginal image quality (in the middle), and high or good image quality (on the right). As shown in FIG. 8C, the display concept 802 shows the right most indicator for the visual signal 828, indicating a good image quality for the image 820. Furthermore, the label 822 includes the text "good image," where the good image is classified as described above.

FIG. 8D shows a display concept 803 of another display of the image 820, the visual signal 828, and an image quality indicator 830 showing a relative image quality of the image 820. The visual signal 828 may show the right-most indicator (which may be colored, e.g., green) representing the good image quality. The image quality indicator 830 may provide an image quality percentage between 0 and 100%. As shown in the display concept 803, the image quality indicator 830 may show an image quality of 87% for the image 820. Similar to the visual legend 824 and the visual signal 828 being able to indicate different image qualities, the image quality indicator 830 may have different thresholds for good, marginal, and poor image qualities. As shown in FIG. 8D, the display concept 803 shows that the image 820 has an image quality of 87% via the image quality indicator 830. The right-most indicator in the visual signal 828 indicates that the image 820 has a good image quality, where the good image quality is classified as described above.

FIG. 8E shows a display concept 804 of another display of the "good" image 820, quality related values 834 for a sequence of images up to and including the image 820, and a graph 832 of the quality of the sequence of images up to and including the image 820. The quality related values 834 show a standard deviation (STD) of the quality value of 22 and an average quality of 63%. The average quality may comprise an average of the image quality 830 values for the images in the sequence of images up to and including the image 820. Furthermore, the graph 832 shows how at least a subset of the sequence of images compare to each other, for example, with respect to the quality related values 834. In some embodiments, the graph 832 is a real-time graph scaled until it reaches a pre-defined number of images and may scroll as additional images are added to the sequence of images.

FIG. 8F shows a display concept 805 of a display of a "bad" image 840, the label 822, and the image quality indicator 830 showing a relative image quality of the image 840. The label 822 indicates that the image 840 is a "bad" image and further indicates why the image 840 has a bad image quality, which in this case is because bubble artifacts are detected in the image 840. The classification of "bad image" is for the image 840 as a whole and indicates that one or more artifacts are present in the image 840. As introduced above, the label 822 may comprise the textual label that uses one or more words to describe the image quality of the image 840, evaluated based on whether the imaging system is able to process the corresponding image for the one or more measurements of the patient's eye. Thus, when the image 840 is a bad image, then the label 822 may identify the image 840 as a "Bad Image" with details as to what caused the image 840 to have the bad image quality. The image quality indicator 830 in this example provides the image quality of 32% for the image 840.

FIG. 8G shows a display concept 806 of another display of the "bad" image 840, where in this example the label 822 identifies the image quality of the image 840 and the visual legend 824 shows a relative image quality of the image 840. The visual legend 824 may comprise the range of colors, hues, grayscales, patterns, and/or the like introduced above. The visual legend 824 may include the arrow 826 that indicates where the image quality of the image 840 falls on the visual legend 824. In FIG. 8G, the arrow 826 identifies the first level in the visual legend 824, thereby indicating that the image 840 is a bad image. The label 822 includes the text "Bad Image," where the bad image is classified as described above, and includes additional text identifying the type of artifact(s) identified in the image 840.

FIG. 8H shows a display concept 807 of another display of the "bad" image 840, where in this example the label 822 identifies the image quality of the image 840 and the visual signal 828 shows the relative image quality of the image 840. The visual signal 828 may comprise the different colors, hues, grayscales, patterns, and/or the like indicating different information about the image 840, as introduced above. As shown in FIG. 8H, the display concept 807 shows that the left-most indicator for the visual signal 828, indicating the bad image quality for the image 840. Furthermore, the label 822 includes the text "bad image," where the bad image is classified as described above, and includes additional text identifying the type of artifact(s) identified in the image 840.

FIG. 8I shows a display concept 808 of another display of the "bad" image 840, where in this example the visual signal 828 and the image quality indicator 830 show the relative image quality of the image 840. For example, the visual signal 828 may show the left-most indicator representing the bad image quality for the image 840. The image quality indicator 830 provides an image quality percentage of 17% for the image 840.

FIG. 8J shows a display concept 809 of another display of the "bad" image 840, the quality related values 834 for the sequence of images up to and including the image 840, and the graph 832 of the quality of the sequence of images up to and including the image 840. The quality related values 834 show a STD quality value of 22 and an average quality of 14%. The average quality may comprise an average of the image quality 830 values for the images in the sequence of images up to and including the image 840. Furthermore, the graph 832 shows how at least a subset of the sequence of images compare to each other, for example, with respect to the quality score and/or the average quality 834. In some embodiments, the graph 832 is a real-time graph scaled until it reaches a pre-defined number of images and may scroll as additional images are added to the sequence of images.

FIG. 8K shows a display concept 810 of a display of the "bad" image 840, the label 822, the image quality indicator 830 showing a relative image quality of the image 840, and one or more circles 837 identifying approximate locations of the bubble artifacts in the image 840. The circles 837 may comprise one or more colors, hues, grayscales, patterns, and/or the like to identify between different artifacts and/or acceptability of artifacts. For example, following the discussion above, the different colors, hues, grayscales, patterns, and/or the like of the circles 837 may correspond to different ranges of artifacts, from unacceptable or bad artifacts, to marginal artifacts, to acceptable artifacts. The label 822 indicates that the image 840 is the "bad" image and further indicates why the image 840 is identified as bad (e.g., that the bubble artifacts are detected). The image quality indicator 830 may provide the image quality percentage of 32% for the image 840.

FIG. 8L shows a display concept 811 of a display of the "bad" image 840, the label 822, the image quality indicator 830 showing a relative image quality of the image 840, and one or more circles with transparent fill 838 identifying approximate locations of the bubble artifacts in the image 840. As introduced above, the circles with transparent fill 838 may comprise one or more colors, hues, grayscales, patterns, and/or the like to identify between different artifacts and/or acceptability of artifacts. For example, following the discussion above, the different colors, hues, grayscales, patterns, and/or the like of the circles with transparent fill 838 may correspond to different ranges of artifacts, from unacceptable or bad artifacts, to marginal artifacts, to acceptable artifacts. The label 822 indicates that the image 840 has the "bad" image quality and further indicates why the image 840 is bad (e.g., that bubble artifacts are detected). The image quality indicator 830 may provide the image quality percentage of 32% for the image 840.

FIG. 8M shows a display concept 812 of another display of the "bad" image 840, the label 822 identifying the image quality of the image 840, the visual legend 824 showing the relative image quality of the image 840, and individual text descriptions 839 for called out artifacts. The visual legend 824 may comprise the range of colors, hues, grayscales, patterns, and/or the like introduced above. The visual legend 824 may include the arrow 826 that indicates where the image 840 falls on the visual legend 824. In FIG. 8M, the arrow 826 indicates that the image 840 is a bad image when the arrow 826 identifies the low value in the visual legend 824. The label 822 includes the text "Bad image" and descriptions of "Bubble Artifacts Detected" where the bad image is classified as described above, identifying the type of artifact(s) identified in the image 840. The individual text descriptions 839 can include various details of the identified artifacts, including size, relative locations, impact on the quality of the image, acceptability, and the like. As shown in the display concept 812, the individual text descriptions 839 are associated with identified artifacts using lead lines, or the like.

FIG. 8N shows a display concept 813 of another display of the "bad" image 840, the label 822 identifying the image quality of the image 840, the visual legend 824 showing the relative image quality of the image 840, and individual text descriptions 839 for called out artifacts. The visual legend 824 may comprise the range of colors, hues, grayscales, patterns, and/or the like introduced above. The visual legend 824 may include the arrow 826 that indicates where the image 840 falls on the visual legend 824. In FIG. 8N, the arrow 826 indicates that the image 840 has a bad image quality when the arrow 826 identifies the low level in the visual legend 824. The label 822 includes the text "Bad image" and descriptions of "Bubble Artifacts Detected" where the bad image is classified as described above, identifying the type of artifact(s) identified in the image 840. The individual text descriptions 839 can include various details of identified artifacts, including size, relative locations, impact on the quality of the image, acceptability, and the like. As shown in the display concept 813, the individual text descriptions 839 are associated with identified artifacts using alphanumeric identifiers, or the like.

FIG. 8O shows a display concept 814 of another display of the "bad" image 840, the quality related values 834 for the sequence of images up to and including the image 840, the graph 832 of the quality of the sequence of images up to and including the image 840, and one or more circles 837 identifying approximate locations of the bubble artifacts in the image 840. The quality related values 834 show a STD quality value of 22 and an average quality of 14%. The average quality may comprise an average of the image quality 830 values for the images in the sequence of images up to and including the image 840. Furthermore, the graph 832 shows how at least a subset of the sequence of images compare to each other, for example, with respect to the quality related values 834. In some embodiments, the graph 832 is a real-time graph scaled until it reaches a pre-defined number of images and may scroll as additional images are added to the sequence of images. Furthermore, the circles 837 may comprise one or more colors, hues, grayscales, patterns, and/or the like to identify between different artifacts and/or acceptability of artifacts. For example, following the discussion above, the different colors, hues, grayscales, patterns, and/or the like of the circles 837 may correspond to different ranges of artifacts, from unacceptable or bad artifacts, to marginal artifacts, to acceptable artifacts.

In some embodiments, graphical identification of artifact locations in an image sequence are based on hysteresis. That is, from image to image of the sequence, a given artifact, for example a bubble, may generally be located at the same or substantially the same location as compared to the previous and/or subsequent image(s). These locations may be subject to numerical quantization and other noise factors that slightly change or modify the location values from one image to the other. Through hysteresis, the artifact's location graphic, for example the color coded circle overlays introduced above, on the image display is not updated unless the difference between the previous location and the current location exceeds some threshold. The use of the hysteresis may prevent a distracting, visible jitter in the location of image artifacts during a real-time display of the image sequence. This hysteresis may also apply to numerical data and text descriptions, such as "good image" and "bad image".

In some embodiments, the location of specific artifacts in the displayed image is indicated in various ways. The artifacts may be displayed either in real-time or only for static images, for example, based on a selection by the operator. In some embodiments, option sets, for example, as set up by an individual operator, may be specified so that display options are retained between exams and/or procedures and the operator does not need to select them for each patient. In addition, various operating modes (for example, a novice mode and/or an expert mode) may exist so that different levels of help and/or identification are provided to the operator based on the operating mode selected or activated for the procedure or operator. In some embodiments, along with the text display of artifact description, such as "bubble", identified artifacts can be displayed with numeric values for both individual and overall artifacts. Such text displays of artifact descriptions can include values for severity (for example, quality score) and area of the artifacts. In some embodiments, an overall artifact value includes a total image quality score, a total number of artifacts in the image, a number of each type of artifact, an overall area affected by artifacts, and the like.

Example Clauses

Implementation examples are described in the following numbered clauses:

Clause 1: A system for processing image data from an intraoperative diagnostic device in real-time during an ophthalmic procedure, the system comprising: an image capture element configured to capture a grayscale image of a patient's eye from the intraoperative diagnostic device, the grayscale image having a first size; an image processing element configured to: obtain the grayscale image from the image capture element; scale the grayscale image from the first size to a second size; and preprocess the scaled grayscale image in preparation for classification; a two-stage classification model comprising: a feature extraction stage configured to process the scaled grayscale image and generate a feature vector based on the scaled grayscale image, and a classification stage configured to process the feature vector and generate an output vector based on the feature vector; wherein the image processing element is further configured to determine an image quality of the obtained grayscale image based on the output vector of artifact probabilities for display to an operator, and wherein the image quality of the obtained grayscale image indicates a probability that the obtained grayscale image includes an artifact.

Clause 2: The system of Clause 1, further comprising a data display element configured to generate a display of the image quality of the obtained grayscale image to the operator.

Clause 3: The system of Clause 2, wherein the data display element is further configured to display the obtained grayscale image based on a determination that the grayscale image includes the artifact and that the artifact reduces the image quality of the obtained grayscale image below a threshold.

Clause 4: The system of Clause 3, wherein the data display element is further configured to generate the display of the obtained grayscale image with an indicator identifying a location of the artifact in the obtained grayscale image based on the determination that the grayscale image includes the artifact that reduces the image quality below the threshold.

Clause 5: The system of Clause 4, further comprising at least one of an image segmentation model or an object detection model configured to identify the location of the artifact for display to the operator based on the obtained grayscale image.

Clause 6: The system of any one of Clauses 2-5, wherein: the data display element is further configured to display: a first indicator indicating an overall quality display relative to an average of image qualities of a subset of images being processed; and a second indicator indicating the image quality for the obtained grayscale image; and the image quality for the obtained grayscale image is based on a probability that the artifact exists in the scaled and preprocessed grayscale image.

Clause 7: The system of any one of Clauses 1-6, wherein: in order to preprocess the scaled grayscale image, the image processing element is further configured to create a set of three scaled grayscale images, and in order to process the scaled grayscale image and generate a feature vector based on the scaled grayscale image, the feature extraction stage is further configured to generate the feature vector based on the set of three scaled grayscale images, wherein each scaled grayscale image of the set of three grayscale images is used as an input data channel to the feature extraction stage.

Clause 8: The system of any one of Clauses 1-7, wherein: the feature extraction stage comprises a convolutional neural network, and the classification stage comprises one or more fully connected layers and a sigmoid activation function.

Clause 9: The system of any one of Clauses 1-8, wherein: the obtained grayscale image comprises a wide field of view image type and the artifact is caused by one or more of debris or an instrument, the obtained grayscale image comprises focus view image type and the artifact is caused by one or more of drying or excess fluid at a location of the patient's eye, or the obtained grayscale image comprises an interferogram view image type and the artifact comprises one or more of a glint, a bubble, or a floater in the obtained grayscale image.

Clause 10: The system of Clause 9, further comprising: a second two-stage classification model comprising: a second feature extraction stage configured to process a second scaled grayscale image and generate a second feature vector based on the second grayscale image; and a second classification stage configured to process the second feature vector and generate a second output vector based on the second feature vector, and a third two-stage classification model comprising: a third feature extraction stage configured to process a third scaled grayscale image and generate a third feature vector based on the third grayscale image; and a third classification stage configured to process the third feature vector and generate a third output vector based on the third feature vector, wherein: the scaled grayscale image processed by the feature extraction stage comprises a first of the wide field of view image type, the focus view image type, and the interferogram view image type, the second grayscale image processed by the second feature extraction stage comprises another of the wide field of view image type, the focus view image type, and the interferogram view image type, and the third grayscale image processed by the third feature extraction stage comprises the third of the wide field of view image type, the focus view image type, and the interferogram view image type not processed by the feature extraction stage and the second feature extraction stage.

Clause 11: The system of Clause 10, wherein the scaled grayscale image is processed by the feature extraction stage in parallel with the second grayscale image being processed by the second feature extraction stage and the third grayscale image being processed by the third feature extraction stage.

Clause 12: The system of any one of Clauses 10 and 11, wherein the scaled grayscale image is processed by the feature extraction stage in series with the second grayscale image being processed by the second feature extraction stage, which is processed in series with the third grayscale image being processed by the third feature extraction stage.

Clause 13: The system of any one of Clauses 1-13, wherein the intraoperative diagnostic device is configured to perform refractive analysis on the images.

Clause 14: The system of any one of Clauses 1-14, wherein the image processing element is further configured to exclude the grayscale image from further processing when the image quality is below a first threshold based on the artifact.

Clause 15: A method of processing image data obtained from an intraoperative diagnostic device in real-time during an ophthalmic procedure, the method comprising: capturing a grayscale image of a patient's eye from the intraoperative diagnostic device, the grayscale image having a first size; obtaining the grayscale image from an image capture element; preprocessing the grayscale image in preparation for classification by a two-stage machine learning model; generating a feature vector based on the preprocessed grayscale image with a feature extraction stage of the two-stage machine learning model; generating an output vector based on the feature vector with a classification stage of the two-stage machine learning model; and determining an image quality of the obtained grayscale image based on the output vector for display to an operator, wherein the image quality of the obtained grayscale image indicates a probability that the obtained grayscale image includes an artifact that interferes with a measurement by the intraoperative diagnostic device.

Clause 16: The method of Clause 15, further comprising: generating a display of the quality of the obtained grayscale image to the operator; and identifying a location of the artifact in the obtained grayscale image based on a determination that the scaled grayscale image includes the artifact that reduces the image quality below the first threshold.

Clause 17: The method of any one of Clauses 15 and 16, wherein preprocessing the grayscale image comprises scaling the grayscale image from the first size to a second size.

Clause 18: The method of Clause 17, wherein: preprocessing the scaled grayscale image further comprises replicating the scaled grayscale image to create a set of three scaled grayscale images, and generating a feature vector based on the scaled grayscale image comprises generating the feature vector based on the set of three scaled grayscale images, wherein each scaled grayscale image of the set of three grayscale images is used as an input data channel to the feature extraction stage.

Clause 19: The method of any one of Clauses 15-18, wherein: the feature extraction stage comprises a convolutional neural network, and the classification stage comprises one or more fully connected layers and a sigmoid activation function.

Clause 20: The method of any one of Clauses 15-19, wherein: the obtained grayscale image comprises a wide field of view image type and the artifact is caused by one or more of debris or an instrument, the obtained grayscale image comprises focus view image type and the artifact is caused by one or more of drying or excess fluid at a location of the patient's eye, or the obtained grayscale image comprises an interferogram view image type and the artifact comprises one or more of a glint, a bubble, or a floater in the obtained grayscale image.

Clause 21: The method of Clause 20, further comprising: generating a second feature vector based on a second grayscale image with a second feature extraction stage of a second two-stage machine learning model; generating a second output vector based on the second feature vector with a second classification stage of the second two-stage machine learning model; generating a third feature vector based on a third grayscale image with a third feature extraction stage of a third two-stage machine learning model; and generating a third output vector based on the third feature vector with a third classification stage of the third two-stage machine learning model, wherein: the grayscale image comprises a first of the wide field of view image type, the focus view image type, and the interferogram view image type, the second grayscale image comprises another of the wide field of view image type, the focus view image type, and the interferogram view image type, and the third grayscale image comprises the third of the wide field of view image type, the focus view image type, and the interferogram view image type not processed by the feature extraction stage and the second feature extraction stage.

Clause 22: The method of Clause 21, wherein the feature vector is generated in parallel with the second feature vector and the third feature vector.

Clause 23: The method of any one of Clauses 21 and 22, wherein the feature vector is generated in series with the second feature vector, which is generated in series with the third feature vector.

Clause 24: A method of training a two-stage machine learning model that identifies artifacts in images obtained from an intraoperative aberrometer during an ophthalmic procedure, the method comprising: obtaining the images; generating feature vectors with a feature extraction stage of the two-stage machine learning model for each of the images; generating a feature matrix based on stacking the generated feature vectors; and training a classification stage based on the feature matrix, wherein the trained classification stage generates an output for a processed image indicating a probability that the image includes an artifact.

Clause 25: The method of Clause 24, further comprising training weights of the feature extraction stage.

Clause 26: A processing system, comprising: a memory comprising computer-executable instructions; one or more processors configured to execute the computer-executable instructions and cause the processing system to perform a method in accordance with any one of claims 1-25.

Clause 27: A processing system, comprising means for performing a method in accordance with any one of claims 1-25.

Clause 28: A non-transitory computer-readable medium comprising computer-executable instructions that, when executed by one or more processors of a processing system, cause the processing system to perform a method in accordance with any one of claims 1-25.

Clause 29: A computer program product embodied on a computer-readable storage medium comprising code for performing a method in accordance with any one of Clauses 1-25.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A system for processing image data from an intraoperative diagnostic device in real-time during an ophthalmic procedure, the system comprising:
   an image capture element configured to capture a grayscale image of a patient's eye from the intraoperative diagnostic device, the grayscale image having a first size; and
   an image processing element configured to:
      obtain the grayscale image from the image capture element;
      scale the grayscale image from the first size to generate a scaled grayscale image of a second size; and
      preprocess the scaled grayscale image in preparation for classification; and
   a two-stage classification model comprising:
      a feature extraction stage configured to process the scaled grayscale image and generate a feature vector based on the scaled grayscale image, and
      a classification stage configured to process the feature vector and generate an output vector based on the feature vector;
   wherein the image processing element is further configured to determine an image quality of the grayscale image based on the output vector for display to an operator, and
   wherein the image quality of the grayscale image indicates a probability that the grayscale image includes an artifact.

2. The system of claim 1, further comprising a data display element configured to generate a display of the image quality of the grayscale image to the operator.

3. The system of claim 2, wherein the data display element is further configured to display the grayscale image based on a determination that the grayscale image includes the artifact and that the artifact reduces the image quality of the grayscale image below a threshold.

4. The system of claim 3, wherein the data display element is further configured to generate the display of the grayscale image with an indicator identifying a location of the artifact in the grayscale image based on the determination that the grayscale image includes the artifact that reduces the image quality below the threshold.

5. The system of claim 4, further comprising at least one of an image segmentation model or an object detection model configured to identify the location of the artifact for display to the operator based on the grayscale image.

6. The system of claim 2, wherein:
the data display element is further configured to display:
   a first indicator indicating an overall quality display relative to an average of image qualities of a subset of images being processed; and
   a second indicator indicating the image quality for the grayscale image; and
the image quality for the grayscale image is based on a probability that the artifact exists in the scaled and preprocessed grayscale image.

7. The system of claim 1, wherein:
in order to preprocess the scaled grayscale image, the image processing element is further configured to create a set of three scaled grayscale images, and
in order to process the scaled grayscale image and generate a feature vector based on the scaled grayscale image, the feature extraction stage is further configured to generate the feature vector based on the set of three scaled grayscale images,
wherein each scaled grayscale image of the set of three scaled grayscale images is used as an input data channel to the feature extraction stage.

8. The system of claim 1, wherein:
the feature extraction stage comprises a convolutional neural network, and
the classification stage comprises one or more fully connected layers and a sigmoid activation function.

9. The system of claim 1, wherein:
the grayscale image comprises a wide field of view image type and the artifact is caused by one or more of debris or an instrument,
the grayscale image comprises focus view image type and the artifact is caused by one or more of drying or excess fluid at a location of the patient's eye, or
the grayscale image comprises an interferogram view image type and the artifact comprises one or more of a glint, a bubble, or a floater in the grayscale image.

10. The system of claim 9, further comprising:
a second two-stage classification model comprising:
   a second feature extraction stage configured to process a second scaled grayscale image and generate a second feature vector based on the second scaled grayscale image; and
   a second classification stage configured to process the second feature vector and generate a second portion to the output vector based on the second feature vector, and
a third two-stage classification model comprising:
   a third feature extraction stage configured to process a third scaled grayscale image and generate a third feature vector based on the third scaled grayscale image; and
   a third classification stage configured to process the third feature vector and generate a third portion to the output vector based on the third feature vector,
wherein:
   the scaled grayscale image processed by the feature extraction stage comprises a first of the wide field of view image type, the focus view image type, and the interferogram view image type,
   the second scaled grayscale image processed by the second feature extraction stage comprises another of the wide field of view image type, the focus view image type, and the interferogram view image type, and
   the third scaled grayscale image processed by the third feature extraction stage comprises the third of the wide field of view image type, the focus view image type, and the interferogram view image type not processed by the feature extraction stage and the second feature extraction stage.

11. The system of claim 10, wherein the scaled grayscale image is processed by the feature extraction stage in parallel with the second scaled grayscale image being processed by the second feature extraction stage and the third scaled grayscale image being processed by the third feature extraction stage.

12. The system of claim 10, wherein the scaled grayscale image is processed by the feature extraction stage in series with the second scaled grayscale image being processed by the second feature extraction stage, which is processed in series with the third scaled grayscale image being processed by the third feature extraction stage.

13. The system of claim 1, wherein the intraoperative diagnostic device is configured to perform refractive analysis on the image data.

14. The system of claim 1, wherein the image processing element is further configured to exclude the grayscale image from further processing when the image quality is below a first threshold based on the artifact.

15. A method of processing image data obtained from an intraoperative diagnostic device in real-time during an ophthalmic procedure, the method comprising:
capturing a grayscale image of a patient's eye from the intraoperative diagnostic device, the grayscale image having a first size;
obtaining the grayscale image from an image capture element;
preprocessing the grayscale image in preparation for classification by a two-stage machine learning model;
generating a feature vector based on the preprocessed grayscale image with a feature extraction stage of the two-stage machine learning model;
generating an output vector based on the feature vector with a classification stage of the two-stage machine learning model; and
determining an image quality of the grayscale image based on the output vector for display to an operator,
wherein the image quality of the grayscale image indicates a probability that the grayscale image includes an artifact that interferes with a measurement by the intraoperative diagnostic device.

16. The method of claim 15, further comprising:
generating a display of the image quality of the grayscale image to the operator; and
identifying a location of the artifact in the grayscale image based on a determination that the grayscale image includes the artifact that reduces the image quality below a first threshold.

17. The method of claim 15, wherein preprocessing the grayscale image comprises scaling the grayscale image of the first size to generate a scaled grayscale image of a second size.

18. The method of claim 17, wherein:
preprocessing the scaled grayscale image further comprises replicating the scaled grayscale image to create a set of three scaled grayscale images, and
generating a feature vector based on the scaled grayscale image comprises generating the feature vector based on the set of three scaled grayscale images,
wherein each scaled grayscale image of the set of three scaled grayscale images is used as an input data channel to the feature extraction stage.

19. The method of claim 15, wherein:
the feature extraction stage comprises a convolutional neural network, and
the classification stage comprises one or more fully connected layers and a sigmoid activation function.

20. The method of claim 15, wherein:
the grayscale image comprises a wide field of view image type and the artifact is caused by one or more of debris or an instrument,
the grayscale image comprises focus view image type and the artifact is caused by one or more of drying or excess fluid at a location of the patient's eye, or
the grayscale image comprises an interferogram view image type and the artifact comprises one or more of a glint, a bubble, or a floater in the grayscale image.

21. The method of claim 20, further comprising:
generating a second feature vector based on a second grayscale image with a second feature extraction stage of a second two-stage machine learning model;
generating a second output vector based on the second feature vector with a second classification stage of the second two-stage machine learning model;
generating a third feature vector based on a third grayscale image with a third feature extraction stage of a third two-stage machine learning model; and
generating a third output vector based on the third feature vector with a third classification stage of the third two-stage machine learning model,
wherein:
the grayscale image comprises a first of the wide field of view image type, the focus view image type, and the interferogram view image type,
the second grayscale image comprises another of the wide field of view image type, the focus view image type, and the interferogram view image type, and
the third grayscale image comprises the third of the wide field of view image type, the focus view image type, and the interferogram view image type not processed by the feature extraction stage and the second feature extraction stage.

22. The method of claim 21, wherein the feature vector is generated in parallel with the second feature vector and the third feature vector.

23. The method of claim 21, wherein the feature vector is generated in series with the second feature vector, which is generated in series with the third feature vector.

24. A method of training a two-stage machine learning model that identifies artifacts in an image obtained from an intraoperative aberrometer during an ophthalmic procedure, the method comprising:
obtaining the image;
generating feature vectors with a feature extraction stage of the two-stage machine learning model for the image;
generating a feature matrix based on stacking the generated feature vectors; and
training a classification stage based on the feature matrix,
wherein the trained classification stage generates an output for a processed image indicating a probability that the image includes an artifact.

25. The method of claim 24, further comprising training weights of the feature extraction stage.

* * * * *